(12) United States Patent
Jung et al.

(10) Patent No.: US 9,266,370 B2
(45) Date of Patent: Feb. 23, 2016

(54) DNA MARKING OF PREVIOUSLY UNDISTINGUISHED ITEMS FOR TRACEABILITY

(71) Applicant: APDN (B.V.I.) Inc., Tortola (VG)

(72) Inventors: Lawrence Jung, Forest Hills, NY (US); James A. Hayward, Stony Brook, NY (US); MingHwa Benjamin Liang, East Setauket, NY (US); Abdelkrim Berrada, Lake Ronkonkoma, NY (US)

(73) Assignee: APDN (B.V.I) Inc., Stony Brook, NY (US)

(*) Notice: Subject to any disclaimer, the term of this patent is extended or adjusted under 35 U.S.C. 154(b) by 0 days.

(21) Appl. No.: 14/584,100

(22) Filed: Dec. 29, 2014

(65) Prior Publication Data
US 2015/0107475 A1 Apr. 23, 2015

Related U.S. Application Data

(63) Continuation-in-part of application No. 13/796,663, filed on Mar. 12, 2013, now abandoned, and a continuation-in-part of application No. 13/789,093, filed on Mar. 7, 2013, and a continuation-in-part of application No. 13/648,594, filed on Oct. 10, 2012.

(51) Int. Cl.
*G09F 3/00* (2006.01)
*B41M 3/14* (2006.01)
*G07D 7/14* (2006.01)
*B42D 25/378* (2014.01)

(52) U.S. Cl.
CPC .............. *B41M 3/14* (2013.01); *B42D 25/378* (2014.10); *G07D 7/14* (2013.01); *Y10T 29/49826* (2015.01); *Y10T 29/49885* (2015.01)

(58) Field of Classification Search
CPC ........................................................ G09F 3/00

USPC ............................................................. 427/7
See application file for complete search history.

(56) References Cited

U.S. PATENT DOCUMENTS

| | | | |
|---|---|---|---|
| 2002/0167161 A1* | 11/2002 | Butland | 283/72 |
| 2008/0293052 A1* | 11/2008 | Liang et al. | 435/6 |
| 2009/0075261 A1* | 3/2009 | Hayward et al. | 435/6 |
| 2009/0253127 A1* | 10/2009 | Gaudreau et al. | 435/6 |
| 2009/0286250 A1* | 11/2009 | Hayward et al. | 435/6 |

* cited by examiner

*Primary Examiner* — Cachet Sellman
(74) *Attorney, Agent, or Firm* — Algis Anilionis; F. Chau & Associates, LLC

(57) ABSTRACT

The invention provides a method of marking an item with naturally-derived or synthetic non-natural polymeric marker molecules, such as a DNA or Peptide marker in conjunction with optional visible or rapid scan reporters for authenticating or tracking, in which the method includes providing an item for marking, and applying a medium including a DNA marker to the item. The invention further provides methods for stably binding and immobilizing activated deoxyribonucleic acid onto objects and substrates. The method includes exposing the deoxyribonucleic acid to alkaline conditions, and contacting the deoxyribonucleic acid to the object or substrate. Also provided are methods for increasing the recoverability of taggants from an object. The methods include the steps of incorporating a taggant into a solution; mixing the solution including the taggant with a perturbant to form a first perturbant taggant solution; mixing the first perturbant taggant solution with a polymer to form a second perturbant taggant polymer solution; and applying the second perturbant taggant polymer solution to at least a portion of the object to form a taggant-coated object. The invention also provides a method of marking an item with a DNA marker for authenticating or tracking, in which the method includes providing a medium including a DNA marker, and molding the medium including the DNA marker to provide all or part of the item. The DNA marker encodes information unique to the item and/or the model of the item as desired.

20 Claims, No Drawings

DNA MARKING OF PREVIOUSLY UNDISTINGUISHED ITEMS FOR TRACEABILITY

RELATED APPLICATIONS

This application is a continuation-in-part of U.S. patent application Ser. No. 13/796,663 filed Mar. 12, 2013 and is also a continuation-in-part of U.S. patent application Ser. No. 13/789,093 filed Mar. 7, 2013 and is also a continuation-in-part of U.S. patent application Ser. No. 13/648,594 filed Oct. 10, 2012, the disclosures of each of which are incorporated by reference herein in their entireties.

Society has become increasingly dependent on the proper functioning of complex electronics, electrical systems and mechanical equipment for everyday pursuits. For instance, degradation of safety and reliability of systems has become a major problem. The effective operation of these systems depend on the proper functioning of their components, many of which are obtained from undocumented suppliers and may be subject to replacement with parts from unauthenticated or counterfeit sources.

United States currency, paper financial instruments and checks are routinely subject to scrutiny due to the prevalence of counterfeit notes and forged checks. For instance, recently, authorities and banks recovered at least $7.8 million in fake currency across the U.S. that they believe were manufactured in a single South American country, according to government statistics. Furthermore, almost half a million dollars in fake U.S. cash from the same source was seized before it was spent during that same period, and more than $18.2 million more in raids in the origin country, according to the U.S. Secret Service.

Counterfeit electronics, such as flat screen TVs, Computer products, electronics, disks loaded with computer programs, CDs, DVD and BluRay disks, are especially troubling, since these counterfeit items have also been found to be more likely to also include defects or even malware.

Medical products are also targets for counterfeiting. Losses due to counterfeit pharmaceuticals, medicines and remedies are estimated to amount to over $3 billion per year in the US alone. Unsuspecting users of counterfeit drugs may not be able to differentiate between genuine and fake drugs and may be harmed by these unregulated products.

Nowadays, designer clothing and accessories such as suits, shirts, dresses and blouses, shoes and handbags are often found to be counterfeit, even when purchased from reputable stores. Watches and sports indicia and memorabilia are also subject to counterfeiting. Recently, U.S. Immigration and Customs Enforcement seized $17 million worth of counterfeit NFL merchandise and fake Super Bowl tickets, and made over forty arrests in operation that took five months to complete. The operation also shut down over three hundred websites used to move the false merchandise, and over one hundred and fifty counterfeit tickets valued at about one thousand dollars each were seized. In the weeks before the Super Bowl, counterfeiters flooded the U.S. with fake NFL jerseys. Federal agents scoured T-shirt shops and ecommerce website postings looking for bargain-priced NFL merchandise. Before the Super Bowl, Immigration and Customs Enforcement (ICE) and other agencies confiscated over ten thousand sports-related counterfeit items nationwide, with more seizures occurring through the Super Bowl weekend. The value of the goods if real would be over a million dollars.

Household items such as furniture, carpets, rugs and antiques are not immune from counterfeiting. High value artwork has long been the domain of counterfeiters and forgers. London's famous Victoria and Albert Museum has a separate gallery devoted to first-class fakes and forgeries; and the del Faso museum at the University of Salerno in Southern Italy displays counterfeit artworks, including nearly perfect forgeries of Warhol, Mario Schifano, and other high-priced artists. Italy's military police, the Carabinieri supply the artwork, having collected more than sixty thousand fakes in raids across the country over the last few years, which are on view at the del Faso.

Counterfeit automotive parts, including various aftermarket parts, such as for instance, brake pads, water pumps, wheel hubs and transmission filters, are also often substandard parts made to appear as the premium products produced by well-known auto manufacturers such as Ford, Daimler Chrysler and General Motors.

As counterfeiters become more sophisticated, detection becomes more difficult and resource-intensive. One security approach is to provide the ability for items to be marked in a manner that authenticates the source of supply. The ability of custom botanical DNA markers to provide authentication has been successfully demonstrated when item marking is applied by the original equipment manufacturer (OEM). DNA marking is the "gold standard" for encryption of product information and validation of authenticity and is also now generally accepted as forensic evidence.

DNA marking provides the four principal attributes of a high-security, anti-counterfeiting item marking technology:
(1) Inherent physical properties that cannot be replicated;
(2) Inability to be physically removed and reattached;
(3) Unique identification at the required level of authentication; and
(4) A track and trace system to authenticate marked items.

The physical properties of DNA markers allow for the provision of a unique fingerprint for each item that can be serialized for tracking and tracing. It is important that an anti-counterfeiting technology cannot be removed and re-attached, otherwise the technology is relying on evidence of tampering and the difficulty of removal and re-attachment for its security properties. Serialization and track and trace attributes are characteristics of technology implementation that provide for widespread usage and adequate methodologies for cost-effective, conclusive authentication.

The feasibility, practicality, repeatability, security, and performance of authentication methods using DNA markers depend on one or more of the following characteristics:
- the ability to provide a unique marking technique that cannot be replicated and offering forensic proof of authenticity of the source of supply;
- negligible or zero impact of marking on environmental or any additional personnel safety issues;
- the ability to be integrated into existing production processes;
- the ability to mark small items, such as individual microcircuits;
- a wide variety of types of surface finishes to which marking can be applied;
- substantially zero impact on the technical integrity (such as form, fit, and function) of the item marked;
- the ability to defeat transfer or replication;
- compatibility with confirmatory testing that can be conducted by a reputable, independent laboratory;
- the ability to withstand under extreme environmental conditions, such as those experienced in electronic component production and weapon system operating environments and remain stable; and the availability of processes already in place to ensure marking material is not diverted or misused by manufacturers, distributors, or unrelated third parties.

Branches of the US Government especially the military, have sought techniques and technologies that provide the ability to mark items in a manner that authenticates the source of supply via an unalterable, untamperable means. For instance, in an effort to protect its active military and civilian personnel from the possible catastrophic consequences that could result from the use of counterfeit and other nonconforming items in our weapon systems, certain branches of the U.S. military have mandated the use of deoxyribonucleic acid (DNA) authentication marking for all future procurements of electronic microcircuits.

Applied DNA Sciences, Inc. has been identified as the single known source for a botanical DNA marking technology with proven use in authentication marking by the original equipment manufacturer (OEM) that also has processes in place for quality assurance and authentication or security purposes and is ready for immediate implementation, particularly for application in electronics and other federal supply class items.

Military Applications

Counterfeit electronic devices and components are a serious threat to military service personnel. Detecting counterfeits is an expensive process requiring extensive testing. DNA markers have been recognized as providing the ultimate degree of security of information content for authentication, traceability and tracking. For instance the Defense Logistics Agency (DLA) arm of the U.S. military has issued a policy to expand requirements for DNA authentication marking on items falling within the electronics federal supply class (FSC 5962): Electronic Microcircuits, which have been determined to be at high risk for counterfeiting. DNA marking requirements for manufacturers were implemented in PROCLTR 12-44, which was issued on Aug. 1, 2012, pursuant to the National Defense Authorization Act for Fiscal Year 2012, Section 818, Detection and Avoidance of Counterfeit Electronic Parts. This policy requires contractors to provide items that have been marked with botanically-generated DNA marking material produced by Applied DNA Sciences or its authorized licensees, if any. DLA is initially targeting microelectronics, but the technology is used with other commodities commercially and has broad implications for other products and equipment at risk for counterfeiting. DNA authentication also being applied to six additional department of Defense Federal Supply Groups (FSGs): 1. FSG 59 (Electrical and Electronic Equipment Components); 2. FSG 31 (Bearings); 3. FSG 25 (Vehicular Equipment Components); 4. FSG 29 (Engine Accessories); 5. FSG 47 (Pipe, Tubing, Hose, and Fittings); and 6. FSG 53 (Hardware and Abrasives). See "Defense Standardization Program (DSP) Policies and Procedures available as an electronic file at website: http://www.dsp.dla.mil/APP_UIL/content/policy/docs/4120-24 m.pdf the contents of which are incorporated by reference herein.

SUMMARY

The present invention provides a method of marking an item with a DNA marker for authenticating or tracking, the method includes: providing an item for marking; and applying a medium including a DNA marker to the item. The DNA marker encodes information unique to the item.

The method of applying can be by any suitable method of application, such as by, affixing, printing, varnishing, stamping, painting, coating or labeling. The printing can be by any suitable method, such as for instance, by laser jet printing, inkjet printing, Videojet printing, standard printed electronics methods, lithography, flexography, dye transfer printing, laser printing, pad printing, relief printing, rotogravure, screen printing, intaglio printing, offset printing, letterpress printing, electro photography, thermal printing, line printing, dot matrix printing, daisy wheel printing, blueprint printing, solid ink printing, 3D printing, or by gang-run printing.

Alternatively, the present invention provides a method of marking an item with a DNA marker for authenticating or tracking, the method includes: providing a medium including a DNA marker, and molding the medium including the DNA marker to provide all or part of the item. The DNA marker encodes information unique to the item. For example, the molding of the medium including the DNA marker providing all or part of the item may be performed by any suitable manual or automated molding method, such as by blow molding, compaction and sintering, expanded bead molding, extrusion molding, foam molding, injection molding, laminating, reaction injection molding, matched molding, matrix molding, plastic molding, pressure plug assist molding, rotomolding, transfer molding, thermoforming, vacuum forming, vacuum plug assist molding or by conformal coating.

The present invention provides methods of immobilizing a deoxyribonucleic acid to a substrate or of binding a deoxyribonucleic acid to a substrate. The method includes exposing the deoxyribonucleic acid to alkaline pH, and contacting the alkaline exposed deoxyribonucleic acid to the substrate.

One embodiment of the present invention provides a method of binding of a deoxyribonucleic acid to a substrate, wherein the method includes exposing the deoxyribonucleic acid to alkaline conditions wherein the alkaline conditions are produced by mixing the deoxyribonucleic acid with an alkaline solution having a high pH (such as for instance a pH of about 9.0 to about 14.0), and contacting the alkaline-exposed deoxyribonucleic acid to the substrate. In one embodiment, the alkaline solution is a solution of a hydroxide of an alkali metal.

In another embodiment of the present invention, the alkaline solution is a solution of a high pH buffer. In another embodiment, the high pH buffer is selected from the group consisting of CABS (4-[cyclohexylamino]-1-butanesulphonic acid), CAPS (N-cyclohexyl-3-amino-propanesulfonic acid), AMP (2-amino-2-methyl-1-propanol), CAPSO (N-cyclohexyl-2-hydroxyl-3-aminopropanesulfonic acid), CHES (2-(N cyclohexylamino) ethanesulphonic acid), AMPSO (3-[(1,1-dimethyl-2-hydroxyethyl)amino]-2-hydroxypropanesulfonic acid) and a mixture of any two or more of the foregoing.

In another embodiment, an object marked with marker DNA in which the marker DNA is an alkaline pH activated DNA bound to the object is provided In another embodiment, the alkaline pH activated DNA is bound to a material selected from the group consisting of cotton, wool, nylon, plastic, metal, glass, wood, printing ink and a pharmaceutical composition.

In an embodiment, the object marked with the marker DNA includes one of a pharmaceutical tablet, a pharmaceutical capsule, or a pharmaceutical powder.

Exemplary embodiments of the present invention provide a methodology for extraction of taggants from a tagged article surface without damaging the article or disturbing the aesthetics of its appearance.

In an exemplary embodiment of the present invention, a method for facilitating the inclusion of traceable taggants into a polymer matrix useful for coating an object is provided. The method includes incorporating a taggant into a solution, mixing the solution including the taggant with a perturbant to form a first perturbant taggant solution, mixing the first perturbant taggant solution with a polymer to form a second perturbant taggant solution and applying the second perturbant taggant solution to at least a portion of the object to form a taggant-coated portion of the object.

In another exemplary embodiment, the invention provides a method for increasing recoverability of traceable taggants incorporated into a polymer matrix in a coating of an object. The method includes incorporating a taggant into a solution, mixing the solution including the taggant with a perturbant to form a first perturbant taggant solution, mixing the first perturbant taggant solution with a polymer to form a second perturbant taggant solution and applying the second perturbant taggant solution to at least a portion of the object, wherein the recovery of the taggant is enhanced by the perturbant.

In still another exemplary embodiment of the present invention, a method for authenticating an object is provided. The method includes providing an object comprising a coating that includes a taggant such as a nucleic acid, a perturbant such as a polyol and a polymer coating; recovering the taggant from the object and verifying the authenticity of the object by identifying the taggant.

In accordance with another exemplary embodiment of the present invention, an object marked with a taggant is provided. The object can include a coating covering at least a portion of the surface of the object of interest; wherein the coating comprises a nucleic acid taggant and a perturbant in a polymer. Alternatively, the object can include a nucleic acid taggant and a perturbant in a polymer uniformly distributed throughout the object. In another alternative, the object may include the nucleic acid taggant and a perturbant in a polymer non-uniformly distributed in the object, such as in a portion of a coating and/or in a portion of the object that does not include a surface coating.

In accordance with yet another embodiment of the present invention, a method for authenticating an object is provided. The method includes providing an object having a coating that includes a taggant, at least one perturbant, such as a polyol, recovering the taggant from the object and verifying the authenticity of the object by identifying the taggant by any of the well known methods described in detail below.

In accordance with another embodiment of the present invention, an object marked with a taggant is provided. The marked object includes a coating comprising a nucleic acid taggant, at least one perturbant (such as a polyol) and a solvent; the coating may be cured and/or dried to provide a coated object incorporating a taggant and the polyol or polyols and any residual solvent after the curing and/or drying steps.

DETAILED DESCRIPTION

Before the present methods for authenticating products are described, it is to be understood that this invention is not limited to particular product described, as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated by reference herein to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a taggant" includes a plurality of such taggants and reference to "the primer" includes reference to one or more primers and equivalents thereof known to those skilled in the art, and so forth.

If any publications are discussed here, they are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

"Optional" or "optionally" means that the subsequently described event or circumstance may but need not occur, and that the description includes instances where the event or circumstance occurs and instances in which it does not.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Solvates" of compounds means forms of the compounds that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The term "emitting reporter" means a chemical substituent or material that produces, under appropriate excitation conditions, a detectable optical signal. The optical signal produced by an emitting reporter is typically electromagnetic radiation in the near-infrared, visible, or ultraviolet portions of the spectrum. The emitting reporters of the invention are generally up-converting reporters, but can also be for example, fluorescent and colorimetric substituents.

The term "phosphor particle" means a particle or composition comprising at least one type of upconverting phosphor material.

The term "primer" means a nucleotide with a specific nucleotide sequence which is sufficiently complimentary to a particular sequence of a target DNA molecule, such that the primer specifically hybridizes to the target DNA molecule. In some embodiments, the primer can be extended by chain elongation for sequencing, or can be used for dot blot hybridization. In other embodiments, at least a 3' portion of the primer sequence is complementary to the target DNA molecule so that the 3' end can be extended for DNA sequencing.

The term "probe" refers to a binding component which binds preferentially to one or more targets (e.g., antigenic epitopes, polynucleotide sequences, macromolecular receptors) with an affinity sufficient to permit discrimination of labeled probe bound to target from nonspecifically bound labeled probe (i.e., background).

The term "probe polynucleotide" means a polynucleotide that specifically hybridizes to a predetermined target polynucleotide.

The term "oligomer" refers to a chemical entity that contains a plurality of monomers. As used herein, the terms "oligomer" and "polymer" are used interchangeably. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure.

The term "PCR" refers to polymerase chain reaction. This refers to any technology where a nucleotide is amplified via a temperature cycling techniques in the presence of a nucleotide polymerase, usually a DNA polymerase. This includes but is not limited to real-time PCR technology, reverse transcriptase-PCR, and standard PCR methods. Other relevant technologies include peptide, oligopeptide and protein sequencing by known methods such as Edman degradation and ninhydrin staining.

The term "nucleic acid" means a polymer composed of nucleotides, e.g. deoxyribonucleotides or ribonucleotides, or compounds produced synthetically which can hybridize with naturally occurring nucleic acids in a sequence specific manner analogous to that of two naturally occurring nucleic acids, e.g., can participate in hybridization reactions, i.e., cooperative interactions through Pi electrons stacking and hydrogen bonds, such as Watson-Crick base pairing interactions, Wobble interactions, etc.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "polynucleotide" or "nucleotide" refer to single or double stranded polymer composed of nucleotide monomers of generally greater than 50 nucleotides in length.

The term "monomer" as used herein refers to a chemical entity that can be covalently linked to one or more other such entities to form an oligomer. Examples of "monomers" include nucleotides, amino acids, saccharides, peptides, and the like.

The term "linker" means a compound or a composition which covalently links a biomolecule to the surface of a coated emitting reporter. For example, but not limited to a silylated coated upconverting phosphor particle linked to a DNA molecule.

The term "identifiable sequence" or "detectable sequence" means a nucleotide sequence which can be detected by hybridization and/or PCR technology by a primer or probe designed for specific interaction with the target nucleotide sequence to be identified. The interaction of the target nucleotide sequence with the specific probe or primer can be detected by optical and/or visual means to determine the presence of the target nucleotide sequence.

A "Nucleic acid tag" or nucleic acid taggant is a nucleic acid oligomer or fragment used to identify or authenticate a particular product. Nucleic acid tag and nucleic acid taggant are interchangeable throughout the specification.

The term "DNA taggant" means a nucleic acid tag which comprises deoxy nucleotides. A DNA taggant maybe double-stranded or single-stranded DNA, linear or circular DNA, cDNA, STR (short tandem repeats) and the like. The DNA taggant may also comprise modification to one or more nucleotides which aid in the identification or detection of the DNA taggant. Other taggants useful in the methods of the present invention include peptide, oligopeptide and protein taggants, which can be detected by assay systems well known to those of skill in the art.

The terms "DNA marker" or "DNA marker compound" or DNA taggant are all used interchangeably herein and mean a marker compound utilized to identify or authenticate a particular product. The marker compound comprises a specific DNA oligomer which is used to authenticate the individual product.

The terms "Pharmaceuticals" or "Pills" or "Drugs" are used interchangeably throughout this patent application. These terms refer to chemical compounds that are consumed as tablets, caplets, gel-caps, capsules or other such tablets that contain one or more chemical compounds. Tablets come in a variety of shapes, sizes and colors to help distinguish them from one another because tablets from different suppliers contain the same medication, and it makes sense for safety reasons to differentiate the configuration to avoid the potential for mix-up in the event of switching between brands. Such a mix-up may lead to severe health risks and could have severe or even lethal consequences.

The terms "Pill packaging" or "Tablet Packaging" refer to containers, from single pill containers to containers that contain thousand of pills.

Nomenclature and Structures

In general, the nomenclature used in this application is based on IUPAC systematic nomenclature. Any open valency appearing on a carbon, oxygen sulfur or nitrogen atom in the structures herein indicates the presence of a hydrogen atom unless indicated otherwise. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure.

The DNA markers of the present invention can encode or be used to correspond to manufacturer information such as for instance and without limitation, a unique serial number of the item, the make and model of the item as well as such detail as the date of manufacture or date of shipping and the identification and provenance of components used in its manufacture. Each component sequence or subsequence of the DNA marker can be used to denote a different item of information relevant to the item or its components. DNA markers can also provide authentication and tracking at any point in the supply chain and in the stream of commerce. In another alternative, new DNA markers can be added by affixing or printing with marker DNA encoding new data during manufacture or in the stream of commerce for maintenance of a continuous record of chain of custody of the item.

DNA markers, such as botanical-DNA based markers for security and authentication uses can help protect products, brands and intellectual property of companies, governments and consumers from theft, counterfeiting, fraud and diversion. These DNA markers have an almost unlimited coding capacity which essentially cannot be reverse engineered, and which provides forensic evidence that can be used in the prosecution of thieves, counterfeiters and perpetrators of fraud and diversion.

DNA marking for security and authentication is readily applied to mass produced items such as microelectronic components due to the ease with which the DNA marker can be applied by a wide variety of printing methods using manual, automated or semi-automated equipment. These printing methods include pad printing, inkjet printing, video jet printing, stamping and the like. In one alternative, the DNA marker or markers, such as botanical-DNA based markers can be printed or affixed to packaging, such as tamper-proof packaging in addition to or instead of marking the packaged item itself.

DNA markers suitable for use in the methods of the present invention can be prepared as described in U.S. Patent application publication No. 2008-0299559 A1. Briefly, in certain embodiments, the DNA marker, (interchangeably referred to as a nucleic acid taggant) is derived from DNA extracted from a specific plant source and is specifically digested and ligated to generate artificial nucleic acid sequences which are unique to the world. The digestion and ligation of the extracted DNA is completed by standard restriction digestion and ligase techniques known to those skilled in the art of molecular biology. An optical reporter marker deposited on the item along with the DNA marker also enables the authentication of the article of interest by both confirming that the correct emission spectra/wavelength for the optical reporter is detected as well as facilitating the location of the DNA marker, enabling sequencing if the nucleic acid taggant comprises the correct nucleic acid sequence. The optical reporter marker may camouflage or "hide" a specified nucleic acid tag of verifiable sequence by including extraneous and nonspecific nucleic acid oligomers/fragments, thus making it difficult for unauthorized individuals such as forgers to identify the sequence of the nucleic acid tag. The optical reporter marker can include a specified double-stranded DNA taggant from a known source (such as a mammal, invertebrate, plant or the like) along with genomic DNA from the corresponding or similar DNA source. The amount of the DNA taggant found in a optical reporter marker compound may vary depending on the article to be authenticated, the duration or shelf-life the taggant needs to be viable (e.g. 1 day, 1 month, 1 year, multiple years) prior to authentication, expected environmental exposure, the detection method to be utilized, and other factors.

Other reporters useful in the practice of the present invention include chemical reporters, such as small molecule markers that can be identified with well known and widely available basic chemistry.

In one embodiment, the DNA sequence of the marker DNA is encoded in an encrypted digital code such as for instance a bar code or other visually readable or instrument-readable code, as disclosed in U.S. Provisional Patent Application No. 61/644,939 filed May 9, 2012.

The DNA markers may be synthetically produced using a nucleic acid synthesizer or by isolating nucleic acid material from yeast, human cell lines, bacteria, animals, plants and the like. In certain embodiments, the nucleic acid material may be treated with restriction enzymes and then purified to produce an acceptable nucleic acid marker(s). The length of the nucleic acid marker/tag usually ranges between about 100 to about 10 kilo bases, more usually about 500 bases to about 6 kb, and preferably about 1 kb to about 3 kb in length.

The DNA markers may comprise one specific nucleic acid sequence or alternatively, may comprise a plurality of various nucleic acid sequences. In one embodiment, polymorphic DNA fragments of the type short tandem repeats (STR) or single nucleotide polymorphisms (SNP) are utilized as an anti-counterfeit nucleic acid tag. While the use of a single sequence for a nucleic acid marker may make detection of the marker easier and quicker, the use of a plurality of nucleic acid sequences such as STR and SNP, in general, give a higher degree of security against forgers.

The nucleic acid (NA) taggant may be DNA, cDNA, or any other nucleic acid fragment comprising nucleic acids or nucleic acid derivatives. The NA maybe a nucleic acid fragment that is single stranded or preferably double stranded and may vary in length, depending on the item to be labeled as well as the detection technique utilized in the nucleic acid detection process.

In certain embodiments of the methods of the invention, the nucleic acid taggant is derived from DNA extracted from a specific plant source and is specifically digested and ligated to generate artificial nucleic acid sequences which are unique to the world. The digestion and ligation of the extracted DNA is completed by standard restriction digestion and ligase techniques known to those skilled in the art of molecular biology.

In certain embodiments of the methods of the invention, the nucleic acid marker is derived from DNA extracted from a specific plant source and is specifically digested and ligated to generate artificial nucleic acid sequences which are unique to the world. The digestion and ligation of the extracted DNA is completed by standard restriction digestion and ligase techniques known to those skilled in the art of molecular biology. Once the modified DNA taggant has been produced, the taggant is encapsulated into materials for protection against UV and degradation.

The marker compound maybe produced as a solid or liquid, water or oil based, a suspension, an aggregate and the like. One feature of the marker compounds in some embodiments is to protect the nucleic acid fragment from UV and other degradation factors that may degrade the nucleic acid taggant over time, while the nucleic acid is acting as an authentication tag for a particular product. In certain embodiments, when the taggant is DNA, the nucleic acid tag may be encapsulated and suspended in a solvent solution (aqueous or organic solvent solution) producing a "stock" DNA taggant solution at a specified concentration. This stock DNA solution can then easily be added to the marker compound mixture at an appropriate concentration for the type of product to be authenticated. In certain instances, the DNA taggant maybe mixed with other components of the marker compound without any prior encapsulation. Several processes such as nucleic acid fragment encapsulation and other techniques utilized for protecting nucleotides, and in particular, DNA from degradation, are well known in the art.

Useful methods for the practice of the invention with DNA markers linked to up-converting phosphor particles are also disclosed in U.S. Patent application publication Nos. 2008-0293052 A1; 2008-0299667 A1; 2009-0042191 A1; and 2009-0075261 A1. The DNA markers can be linked to optical reporters for ease of location in or on the item to be marked. The optical reporter can be any suitable optical reporter, such as for instance, a fluorescent compound, a dye, a phosphorescent compound or an up-converting phosphor as disclosed in U.S. Pat. No. 8,124,333.

The optical reporter particle is a light emitting optical reporter and in most embodiments is an upconverting phosphor particle (UCP). In certain embodiments the upconverting phosphor particle UCP is coated with a silylation composition which is configured to covalently link to the nucleic acid taggant. Specific UCPs usable for use in the markers and methods of the invention are described in more detail below.

The optical reporter marker compound may be produced as a solid or liquid, water or oil based, a suspension, an aggregate or the like. The optical reporter marker allows for easy detection of where the optical reporter marker is located on or within the item of interest with basic high intensity light emitting equipment such as a hand-held ultraviolet (UV) lamp, IR emitting diode, hand-held IR laser and the like.

The optical reporter marker also enables the authentication of the item or ink of interest by both confirming that the correct emission spectra/wavelength for the optical reporter particle is detected as well as being able to locate and determine by sequencing if the nucleic acid taggant comprises the correct nucleic acid sequence.

In some embodiments, rare earth-doped ceramic particles are used as phosphor particles to serve as optical reporters. Phosphor particles may be detected by any suitable method, including but not limited to up-converting phosphor (UCP) technology, in which up-converting phosphors transfer lower energy infrared (IR) radiation into higher-energy visible light. Although an understanding of the mechanism is not necessary to practice the present invention and the present invention is not limited to any particular mechanism of action, in some embodiments the UCP particles up-converts infrared light to visible light by multi-photon absorption and subsequent emission of dopant-dependant phosphorescence (See, for instance: U.S. Pat. No. 6,399,397; van De Rijke, et al., Nature Biotechnol. 19(3):273-6 (2001); Corstjens, et al., IEE Proc. Nanobiotechnol. 152(2):64 (2005).

Incorporation of Functional Groups

In certain embodiments, the nucleic acid tag is labeled with at least one compound or "detection molecule" such as, for example, an optical reporter prior to being incorporated into the specified product to aid in the extraction and/or detection of the nucleic acid marker from the product after being placed in a supply chain. A detection molecule is a molecule or compound with at least one functionality. For example, fluorescent molecules, which may be in particulate form, may be configured to the nucleic acid marker for certain detection methods which are described in detail below.

In certain preferred aspects, suitable dyes include, but are not limited to, coumarin dyes, xanthene dyes, resorufins, cyanine dyes, difluoroboradiazaindacene dyes (BODIPY), ALEXA dyes, indoles, bimanes, isoindoles, dansyl dyes, naphthalimides, phthalimides, xanthenes, lanthanide dyes, rhodamines and fluoresceins. In other embodiments, certain visible and near Infrared (IR) dyes and IR materials are known to be sufficiently fluorescent and photostable to be detected as single molecules. In this aspect the visible dye, BODIPY R6G (525/545), and a larger dye, LI-COR's near-infrared dye, IRD-38 (780/810) can be detected with single-molecule sensitivity and are used to practice the authentication process described herein. In certain embodiments, suitable dyes include, but are not limited to, fluorescein, 5-carboxyfluorescein (FAM), rhodamine, 5-(2'-aminoethyl) aminonapthalene-1-sulfonic acid (EDANS), anthranilamide, coumarin, terbium chelate derivatives, Reactive Red 4, BODIPY dyes and cyanine dyes.

There are many linking moieties and methodologies for attaching fluorophore or visible dye moieties to nucleotides, as exemplified by the following references: Eckstein, editor, Oligonucleotides and Analogues: A Practical Approach (IRL Press, Oxford, 1991); Zuckerman et al., Nucleic Acids Research, 15: 5305-5321 (1987) (3' thiol group on oligonucleotide); Sharma et al., Nucleic Acids Research, 19: 3019 (1991) (3' sulfhydryl); Giusti et al., PCR Methods and Applications, 2: 223-227 (1993) and Fung et al., U.S. Pat. No. 4,757,141 (5' phosphoamino group via Aminolink™ II available from Applied Biosystems, Foster City, Calif.) Stabinsky, U.S. Pat. No. 4,739,044 (3' aminoalkylphosphoryl group); AP3 Labeling Technology (U.S. Pat. Nos. 5,047,519 and 5,151,507, assigned to E.I. DuPont de Nemours & Co); Agrawal et al, Tetrahedron Letters, 31: 1543-1546 (1990) (attachment via phosphoramidate linkages); Sproat et al., Nucleic Acids Research, 15: 4837 (1987) (5' mercapto group); Nelson et al, Nucleic Acids Research, 17: 7187-7194 (1989) (3' amino group); and the like.

In other embodiments, a nucleic acid probe complementary to the nucleic acid marker is labeled with at least one compound or molecule with functionality to aid in the detection of the nucleic acid tag/marker. The techniques and dyes utilized in labeling the nucleic acid tag or the complementary probe are the same due to the nucleic acid nature of the tag and probe.

The detection molecules of the invention can be incorporated into probe motifs, such as Taqman probes (Held et al., Genome Res. 6: 986-994 (1996), Holland et al., Proc. Nat. Acad. Sci. USA 88: 7276-7280 (1991), Lee et al., Nucleic Acids Res. 21: 3761-3766 (1993)), molecular beacons; Tyagi et al., Nature Biotechnol., 16:49-53 (1998), U.S. Pat. No. 5,989,823, issued Nov. 23, 1999)) scorpion probes (Whitcomb et al., Nature Biotechnology 17: 804-807 (1999)), sunrise probes (Nazarenko et al., Nucleic Acids Res. 25: 2516-2521 (1997)), conformationally assisted probes (Cook, R., copending and commonly assigned U.S. Provisional Application No. 60/138,376, filed Jun. 9, 1999), peptide nucleic acid (PNA)-based light up probes (Kubista et al., WO 97/45539, December 1997), double-strand specific DNA dyes (Higuchi et al, Bio/Technology 10: 413-417 (1992), Wittwer et al, Bio/Techniques 22: 130-138 (1997)) and the like. These and other probe motifs with which the present detection molecules can be used are reviewed in Nonisotopic DNA Probe Techniques, Academic Press, Inc. 1992.

In other embodiments, the molecular beacon system is utilized to detect and quantify the nucleic acid tag from the product of interest. "molecular beacons" are hairpin-shaped nucleic acid detection probes that undergo a conformational transition when they bind to their target that enables the molecular beacons to be detected. In general, the loop portion of a molecular beacon is a probe nucleic acid sequence which is complementary to the nucleic acid marker. The stem portion of the molecular beacon is formed by the annealing of arm sequences of the molecular beacon that are present on either side of the probe sequence. A functional group such as a fluorophore (e.g. coumarin, EDNAS, fluorescein, lucifer yellow, tetramethylrhodamine, texas red and the like) is covalently attached to the end of one arm and a quencher molecule such as a nonfluorescent quencher (e.g. DABCYL) is covalently attaches to the end of the other arm. When there is no target (nucleic acid tag) present, the stem of the molecular beacon keeps the functional group quenched due to its close proximity to the quencher molecule. However, when the molecular beacon binds to their specified target, a conformational change occurs to the molecular beacon such that the stem and loop structure cannot be formed, thus increasing the distance between the functional group and the quencher which enables the presence of the target to be detected. When the functional group is a fluorophore, the binding of the molecular beacon to the nucleic acid tag is detected by fluorescence spectroscopy.

In certain embodiments, a plurality of nucleic acid tags with varying sequences are used in labeling a particular product. The different nucleic acid tags can be detected quantitatively by a plurality of molecular beacons, each with a different colored fluorophore and with a unique probe sequence complementary to at least one of the plurality of nucleic acid tags. Being able to quantitate the various fluorophores (i.e. various nucleic acid tags) provides a higher level of authentication and security. It should be noted, that the other functional groups described above useful in labeling nucleic acid probes can also be utilized in molecular beacons for the present invention.

In one embodiment, the invention present provides a method by which DNA and fluorophore can be bound to various substrates. With this method DNA can be bound to materials, resist all kinds of finishing processes, such as washing and cleaning, and yet be safely retrieved in order to authenticate the product. Authentication can occur by several methods. One method involves adding fluorophore to the product, making rapid identification possible, as a UV light could detect the presence of a fluorophore. Another authentication method involves binding DNA to substrates via a chemical linker. A linker often includes a chain of carbon atoms with a reactive functional group at the end. This reactive functional group can be activated to bind covalently to an available group or to the substrate or the product to be marked. This DNA attached to the product is unique to the particular product and therefore acts as its fingerprint, making authentication possible. These methods combined would create a fool proof method of identification, where the fluorescence of the product would be the first level of protection and the DNA would be the second, unique and definite layer that could not be duplicated.

In one embodiment the invention provides botanical DNA markers, SigNature™ DNA (Applied DNA Sciences, Stony Brook, N.Y.) that essentially cannot be copied, and are resistant to various chemical and textile treatments. To ensure adherence, SigNature™ DNA was formulated to be tightly bound to both natural and synthetic fibers and other amorphous material such as wool, cotton, polyesters, such as for instance, nylon and polyethylene terephthalate (PET). These textile fabrics can be marked with SigNature™ DNA during the manufacturing process circumventing the need for any additional steps in marking textiles products. As a proof of concept, various woolen yarns and fabrics were finished using standard protocols and the survivability of the SigNature™ DNA was examined at the point of sale as described in the Examples below. In all textiles tested, SigNature™ DNA was recovered and the products were forensically authenticated. Thus, marking textile products with SigNature™ DNA can provide an economical, reliable, and secure method for marking, branding, and forensically authenticating textile products at the DNA level.

Embodiments of the present invention are listed below as non-limiting examples illustrating the invention, but are not intended to be taken as limits to the scope of the present invention, which will be immediately apparent to those of skill in the art.

Exemplary embodiments provide methods for increasing the recoverability of a taggant from an object without disturbing the appearance of the object. Several exemplary embodiments of the present invention are described in detail below.

Exemplary embodiments of the present invention also provide methods for authenticating an object using taggants that have been incorporated onto an object or into a liquid for binding of an activated DNA taggant.

For example, an exemplary embodiment of the invention provides a method for increasing the recoverability of a taggant from an object; the method includes incorporating a DNA taggant onto the surface of an object or into a liquid for binding of the activated DNA taggant to an object or surface.

Alkaline extraction of DNA from cells of organisms takes advantage of the alkali-stable nature of DNA. Cell membranes are disrupted by treatment with alkali, releasing the cellular contents, and melting the double-stranded the nuclear and mitochondrial DNA to release the single stranded DNA forms. These DNA strands readily re-hybridize, snapping back to their double stranded helical structure that can be isolated from the alkali-treated cellular milieu.

The inventors have surprisingly discovered that alkali treatment of isolated DNA also activates the DNA for covalent binding. Without wishing to be bound by theory, it is believed that alkaline conditions lead to ionization of the free hydroxyls at the 3' ends of the DNA strands. The negatively charged —O⁻ group produced at the 3' end of the DNA is a strong nucleophile, reactive with positively charged groups to form stable covalent bonds, stably binding the DNA.

The invention provides methods of binding of a deoxyribonucleic acid to a substrate: The method includes exposing the deoxyribonucleic acid to alkaline conditions, and contacting the deoxyribonucleic acid to the substrate. The DNA bound to the substrate is available for binding by hybridization probes, PCR amplification and DNA sequencing methods.

In one embodiment, the alkaline conditions are produced by mixing the deoxyribonucleic acid with an alkaline solution having a high pH, for instance the pH of the alkaline solution can be a pH of about 9.0 or higher; a pH of about 10.0 or higher; a pH of about 11.0 or higher, or even a pH of about 12.0 or higher, and contacting the deoxyribonucleic acid that has been exposed to the alkaline conditions with the substrate. In one embodiment, the alkaline solution is a solution of a hydroxide of an alkali metal.

Another embodiment of the present invention provides a method of binding a deoxyribonucleic acid to a substrate, the method including exposing the deoxyribonucleic acid to alkaline conditions, wherein the alkaline conditions are produced by mixing the deoxyribonucleic acid with an alkaline solution, and contacting the deoxyribonucleic acid that has been exposed to the alkaline conditions with the substrate; wherein the alkaline solution is a solution of a hydroxide of an alkali metal and the alkali metal is selected from the group consisting of lithium (Li), sodium (Na), rubidium (Rb), and cesium (Cs).

Another embodiment of the present invention provides a method of binding a deoxyribonucleic acid to a substrate, the method including exposing the deoxyribonucleic acid to alkaline conditions, wherein the alkaline conditions are produced by mixing the deoxyribonucleic acid with an alkaline solution, and contacting the deoxyribonucleic acid that has been exposed to the alkaline conditions with the substrate; wherein the alkaline solution is a solution of an alkali metal hydroxide, wherein the alkali metal hydroxide is selected from the group consisting of lithium hydroxide (LiOH), sodium hydroxide (NaOH) and cesium hydroxide (CsOH). In one embodiment, the alkali metal hydroxide is sodium hydroxide (NaOH).

Another embodiment the invention provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with a solution of an alkali metal hydroxide, wherein the alkali metal hydroxide solution having a concentration of from about 1 mM to about 1.0 M.

Another embodiment the invention provides a method of binding a deoxyribonucleic acid to a substrate, the method including exposing the deoxyribonucleic acid to alkaline conditions and contacting the deoxyribonucleic acid that has been exposed to the alkaline conditions with the substrate; wherein the alkaline conditions are produced by mixing the deoxyribonucleic acid with a solution of an alkali metal hydroxide, the alkali metal hydroxide solution having a concentration of from about 10 mM to about 0.9 M.

Another embodiment the invention provides a method of binding a deoxyribonucleic acid to a substrate, the method including exposing the deoxyribonucleic acid to alkaline conditions and contacting the deoxyribonucleic acid that has been exposed to the alkaline conditions with the substrate; wherein the alkaline conditions are produced by mixing the deoxyribonucleic acid with a solution of an alkali metal hydroxide, the alkali metal hydroxide solution having a concentration of from about 0.1 M to about 0.8 M.

Another embodiment the invention provides a method of binding a deoxyribonucleic acid to a substrate, the method including exposing the deoxyribonucleic acid to alkaline conditions and contacting the deoxyribonucleic acid that has been exposed to the alkaline conditions with the substrate; wherein the alkaline conditions are produced by mixing the deoxyribonucleic acid with a solution of an alkali metal hydroxide, the alkali metal hydroxide solution having a concentration of from about 0.4 M to about 0.8 M.

Another embodiment the invention provides a method of binding a deoxyribonucleic acid to a substrate, the method including exposing the deoxyribonucleic acid to alkaline conditions and contacting the deoxyribonucleic acid that has been exposed to the alkaline conditions with the substrate; wherein the alkaline conditions are produced by mixing the deoxyribonucleic acid with a solution of an alkali metal hydroxide, the alkali metal hydroxide solution having a concentration of about 0.6 M.

Another embodiment of the present invention provides a method of binding of a deoxyribonucleic acid to a substrate, wherein the method includes exposing the deoxyribonucleic acid to alkaline conditions and contacting the alkaline exposed deoxyribonucleic acid to the substrate, wherein the deoxyribonucleic acid is mixed with an alkaline solution having a pH from about 9.0 to about 14.0 and incubated at a temperature of from about 0° C. to about 65° C. to produce the alkaline conditions.

Another embodiment of the present invention provides a method of binding of a deoxyribonucleic acid to a substrate, wherein the method includes exposing the deoxyribonucleic acid to alkaline conditions and contacting the alkaline exposed deoxyribonucleic acid to the substrate, wherein the deoxyribonucleic acid is mixed with an alkaline solution having a pH from about 9.0 to about 14.0 and incubated at a temperature of from about 5° C. to about 55° C. to produce the alkaline conditions.

Another embodiment of the present invention provides a method of increasing binding of a deoxyribonucleic acid to a substrate, wherein the method includes exposing the deoxyribonucleic acid to alkaline conditions and contacting the alkaline exposed deoxyribonucleic acid to the substrate, wherein the deoxyribonucleic acid is mixed with an alkaline solution having a pH from about 9 to about 14 and incubated at a temperature of from about 10° C. to about 45° C. to produce the alkaline conditions.

Another embodiment of the present invention provides a method of increasing binding of a deoxyribonucleic acid to a substrate, wherein the method includes exposing the deoxyribonucleic acid to alkaline conditions and contacting the alkaline exposed deoxyribonucleic acid to the substrate, wherein the deoxyribonucleic acid is mixed with an alkaline solution having a pH from about 9 to about 14 and incubated at a temperature of from about 15° C. to about 35° C. to produce the alkaline conditions.

Another embodiment the invention provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with a solution of an alkali metal hydroxide and incubating the mixture at a temperature of from about 0° C. to about 65° C.

Another embodiment of the invention provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with a solution of an alkali metal hydroxide and incubating the mixture at a temperature of from about 15° C. to about 22° C.

In another embodiment the invention provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with an alkali metal hydroxide solution having concentration of from about 0.1 M to about 1.0 M and incubating the mixture for a period of from about 1 minute to about 6 hours at a temperature of from about 10° C. to about 45° C.

In another embodiment the invention provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with an alkali metal hydroxide solution having concentration of from about 0.1 M to about 1.0 M and incubating the mixture for a period of from about 1 minute to about 6 hours at a temperature of from about 15° C. to about 25° C. to produce the alkaline conditions.

Another embodiment provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with an alkali metal hydroxide solution having concentration of about 0.6 M and incubating the mixture for a period of from about 1 minute to about 6 hours at a temperature of from about 15° C. to about 35° C.

Another embodiment provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with an alkali metal hydroxide solution having concentration of about 0.6 M and incubating the mixture for a period of from about 10 minutes to about 2 hours at a temperature of from about 18° C. to about 22° C. to produce the alkaline conditions.

In one embodiment, the present invention provides a method of binding a deoxyribonucleic acid to a substrate, the method includes exposing the deoxyribonucleic acid to alkaline conditions, wherein the alkaline conditions are produced by mixing the deoxyribonucleic acid with an alkaline solution having a high pH, incubating the mixture and then neutralizing the alkaline solution and contacting the neutralized solution containing the deoxyribonucleic acid that has been exposed to the alkaline conditions with the substrate. In one embodiment, the alkaline solution is a solution of a hydroxide of an alkali metal selected from the group consisting of lithium (Li), sodium (Na), rubidium (Rb), and cesium (Cs).

In another embodiment the present invention provides a method of binding a deoxyribonucleic acid to a substrate, the method includes exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with an alkali metal hydroxide solution, and adding a molar excess of a polyionic polymer.

The polyionic polymer can be any suitable polyionic polymer. In one embodiment the polyanionic polymer is a polyamino acid. The polyamino acid can be a homopolymer of a natural amino acid such as L-lysine, or a homopolymer of a non-naturally occurring amino acid, such as for instance D-lysine. In one embodiment, the polyamino acid homopolymer is selected from the group consisting of polyputrescine, polycadaverine, polyspermidine, and polylysine.

Alternatively, in another embodiment, deoxyribonucleic acid can be mixed with a solution of any suitable high pH buffer to produce the alkaline conditions. The high pH buffer can be any suitable high pH buffer with a pKa in a range of from about 9.0 to about 11.0 or higher. In an embodiment, the pH of the high pH buffer can be, for example, a pH of about 9.0 or higher; a pH of about 10.0 or higher; or a pH of about 11.0 or higher. For example, in another embodiment, deoxyribonucleic acid can be mixed with a suitable high pH buffer such as CABS (4-[cyclohexylamino]-1-butanesulphonic acid) with a useful pH range of about 10.0-11.4 (at 25° C.) and a pKa of about 10.70 (at 25° C.) Product No. C5580 Sigma Aldrich, St. Louis, Mo.; CAPS (N-cyclohexyl-3-aminopropanesulfonic acid) with a useful pH range of about 9.7-11.1 (at 25° C.), a pKa of about 10.56 (at 20° C.), a pKa of about 10.40 (at 25° C.) and a pKa of about 10.02 (at 37° C.) Sigma Aldrich Product Nos. C6070 and C2632; AMP (2-amino-2-methyl-1-propanol) with a useful pH range of about 9.0-10.5 (at 25° C.), a pKa of about 9.70 (at 25° C.) Sigma Aldrich Product Nos. A9199 and A9879; CAPSO (N-cyclohexyl-2-hydroxyl-3-aminopropanesulfonic acid) with a useful pH range of about 8.9-10.3 (at 25° C.), a pKa of about 9.60 (at 25° C.), a pKa of about 9.43 (at 37° C.) Sigma Aldrich Product Nos. C2278 and C8085; CHES (2-(N cyclohexylamino)ethanesulphonic add) with a useful pH range of about 8.60-10.0 (at 25° C.), a pKa of about 9.55 (at 20° C.), a pKa of about 9.49 (at 25° C.) and a pKa of about 9.36 (at 37° C.) Sigma Aldrich Product Nos. C2885 and C8210; AMPSO (3-[(1,1-dimethyl-2-hydroxyethyl)amino]-2-hydroxypropanesulfonic acid) with a useful pH range of about 8.3-9.7 (at 25° C.), a pKa of about 9.00 (at 25° C.), a pKa of about 9.10 (at 37° C.) Sigma Aldrich Product Nos. A6659 and A7585, to produce the alkaline conditions.

In an exemplary embodiment of the present invention, the deoxyribonucleic acid that has been exposed to the alkaline conditions is added as a component of a liquid composition. The liquid composition any be any suitable liquid composition, such as for instance, a printing ink. For example, in one embodiment, the ink may be a heat-curing epoxy-acrylate ink, such as Product No. 4408R or the 970 series Touch Dry® pellet each from Markem®, Keene, N.H. Alternatively, the Artistri® P5000+Series-Pigment Ink from Dupont®, or an Epoxy Acrylate Ink, such as Product No. 00-988, from Rahn USA Corp. can be used.

The taggants of the present invention include, for example, nucleic acid taggants. Nucleic acid is a general term for deoxyribonucleic acid (DNA) or ribonucleic acid (RNA), and can be synthetic, or derived from an animal, a plant, a bacterium, a virus, a fungus, or a synthetic vector or a fragment of any of the above-listed nucleic acids, etc. It should be noted that a synthetic nucleic acid can have a sequence of a naturally occurring nucleic acid of an animal, plant, bacterium, fungus, virus or any other organism or synthetic vector. Alternatively, a synthetic nucleic acid can have a unique sequence not found in nature. It should be understood that such unique non-natural sequences may have stretches of sequences which are found in nature, but the entire non-natural sequence is unique and is not found in any plant, animal or virus or any other natural organism. In particular, the nucleic acid sequence encoding the element of data or indicia encrypted or encoded in the taggant of the invention is a unique, non-natural sequence and thereby is adapted for use in authentication of an object of interest.

The taggant useful in combination with the bound DNA that has been activated by alkaline treatment according to the present invention can be any suitable detectable or traceable taggant, for example, a chemical marker or a biological marker. In an embodiment of the methods of the present invention, the taggant is selected from a UV fluorophore, a ceramic IR marker, other DNA, an amino acid, a peptide, a protein, a lipid, a sugar, a polysaccharide, a pheromone, a scent, a trace element, a rare earth element, or a combination of any two or more thereof.

In an embodiment of the present invention, the taggant includes a nucleic acid. In one embodiment, the taggant consists essentially of DNA and no other significant component useful for identification or authentication.

Alternatively, or in addition, other taggants such as, for example, ultraviolet (UV) taggants, Up Converting Phosphor (UCP) infrared (IR) taggants, UV marker taggants, UV fluorophore taggants, ceramic IR marker taggants, protein taggants, and/or trace element taggants can be used in combination with deoxyribonucleic acid taggants activated by alkaline treatment according to the methods of the present invention. In an exemplary embodiment, the taggants used may include, for example, a combination of DNA taggants, and an IR upconverting phosphor (UCP) taggant. In another exemplary embodiment, the taggants used may include, for example, a combination of DNA taggants, an IR upconverting phosphor (UCP) taggant and a UV taggant. For example, in an exemplary embodiment, the IR (UCP) taggant can be, for example, a green, a blue or a red (UCP) IR taggant, such as for instance the Green IR Marker, Product No. BPP-1069; the Blue UCP, Product No. BPP-1070; or the Red UCP, Product No. BPP-1071 from Boston Applied Technologies Inc., Woburn, Mass.

The solution in which the soluble taggants are dissolved according to the methods of the present invention can include, for example, water, TE buffer (10 mM Tris-HCl, 1 mM EDTA), Tris-glycine buffer, Tris-NaCl buffer, TBE buffer (Tris-borate-EDTA), TAE buffer (Tris-acetate-EDTA) and TBS buffer (Tris-buffered saline), HEPES buffer (N-(2-Hydroxyethyl)piperazine-N'-ethanesulfonic acid), MOPS buffer (3-(N-Morpholino)propanesulfonic acid), PIPES buffer (Piperazine-N,N'-bis(2-ethanesulfonic acid), MES buffer (2-(N-Morpholino)ethanesulfonic acid), PBS (Phosphate Buffered Saline), PBP buffer (sodium phosphate+ EDTA), TEN buffer (Tris/EDTA/NaCl), TBST buffer (Tris-HCl, NaCl, and Tween 20), PBST buffer (Phosphate Buffered Saline with Tween 20) and any of the many other known buffers used in the biological and chemical sciences.

The objects of interest marked with the deoxyribonucleic acid and optional additional taggants according to exemplary embodiments of the present invention include, for example, ceramic surfaces, plastic films, vinyl sheets, antiques, items of jewelry, identification cards, credit cards, magnetic strip cards, paintings, artwork, souvenirs, sports collectibles and other collectibles. The authenticity of these objects can then be verified by identifying the taggants bound or covalently bonded thereon through, for example, methods described in further detail below.

In one embodiment, the surface to which the deoxyribonucleic acid that has been exposed to alkaline conditions is bound can be the surface of an object or item formed of a polymer, such as a polymer selected from the group consisting of polycarbonate (PC), polymethyl methacrylate (PMMA), polyurethane (PU), polystyrene (PS), nylon or polypropylene (PP) all of which are readily commercially available.

In one embodiment, the method of the present invention further includes binding an object with the deoxyribonucleic acid that has been exposed to alkaline conditions according to the methods of the present invention, the deoxyribonucleic acid such that the activated deoxyribonucleic acid is chemically bonded to the object, thereby providing the object with authentication, tracking and anti-counterfeiting functions.

The deoxyribonucleic acid that has been exposed to alkaline conditions that has been applied onto an object provides a traceable deoxyribonucleic acid taggant. The traceable deoxyribonucleic acid taggant can be applied over all or part of the object to be identified, validated, authenticated, or if the object is an item of commerce, the item can be tracked at any point through the stream of commerce.

In another embodiment, the traceable deoxyribonucleic acid is an alkaline pH activated DNA bound to the object.

In another embodiment, the alkaline pH activated DNA is bound to an object including a material selected from the group consisting of cotton, wool, nylon, plastic, metal, glass, wood, printing ink, and a pharmaceutical powder.

In another embodiment, the alkaline pH activated DNA is bound to a plastic material selected from the group consisting of a polycarbonate (PC), a polymethyl methacrylate (PMMA), a polyurethane (PU), a polystyrene (PS), a polyamide, a polypropylene (PP), a polyvinyl chloride (PVC), polysulphone, polyvinilacetate (PVA), polyester (PES), a polyethylene terephthalate (PET), a polyethylene (PE), a benzocyclobutene (BCB), a high-density polyethylene (HDPE), a polyvinylidene chloride (PVDC), a low-density polyethylene (LDPE), a high impact polystyrene (HIPS), an acrylonitrile butadiene styrene (ABS), a phenol formaldehyde resin (PF), a melamine formaldehyde (MF), a polyetheretherketone (PEEK), a polyetherimide (PEI), polyimide (PI), a polyether ketone imide, a polylactic acid (PLA), a polytetrafluoroethylene (PTFE), a polymethyl pentene (PMP), a polyether ketone (PEK), a polyether sulfone (PES), a polyphenylene sulfide (PPS), a polytetrafluoroethylene (PTFE), a fluropolymer, a silicone, an Ionomer, a moldable elastomer, an ethylene vinyl alcohol (EVOH), a methalocene polymer and a polyethylene naphthalate material.

In one embodiment, the object marked with the traceable deoxyribonucleic acid includes a pharmaceutical composition comprising a pharmaceutical tablet, a pharmaceutical capsule, or a pharmaceutical powder.

Another exemplary embodiment of the present invention provides a method for authenticating an object which includes providing an object to which a taggant is bound or covalently bonded, sampling the object for identification, tracking, or verifying the authenticity of the object by identifying the unique traceable deoxyribonucleic acid (DNA) taggant.

In one embodiment, the unique taggant is a DNA taggant having a unique DNA sequence and the unique DNA sequence is stored in a database that matches the unique DNA sequence to the data elements corresponding to the object which is bound to or covalently bonded to the unique taggant. The database can in turn be located on a computer that can be accessed in order to locate, track, authenticate and verify the identity of the tagged object from which the taggant was detected.

DNA taggants useful in the examples described below include any suitable DNA taggant, such as for instance, in one embodiment, the DNA taggant is a double stranded DNA oligomer having a length of between about 40 base pairs and about 1000 base pairs. In other embodiments the DNA taggant is a double stranded DNA oligomer with a length of between about 80 and 500 base pairs. In another embodiment the DNA taggant is a double stranded DNA oligomer having a length of between about 100 and about 250 base pairs. Alternatively, the DNA taggant can be single-stranded DNA or any suitable length, such as between about 40 bases and about 1000 bases; between about 80 and 500 bases; or between about 100 and about 250 bases. The DNA taggant can be natural DNA, whether isolated from natural sources or synthetic; or the DNA taggant can be a synthetically produced non-natural sequence. All or a portion of the DNA may comprise an identifiable sequence.

In one exemplary embodiment, the DNA taggant is identifiable by any suitable detection and/or identification method such as for example, hybridization with a taggant-sequence specific nucleic acid probe, an in situ hybridization method (including fluorescence in situ hybridization: FISH), amplification using a polymerase chain reaction (PCR), such as quantitative/real time PCR and detection of the amplified sequences (amplicons) by any of the variety of standard well known methods.

In another embodiment, the hybridization can be carried out with DNA probes, each having a specific nucleotide sequence capable of hybridizing with its complementary sequence. Different probes may be included, one to each cell or well of an array or matrix so that only the probe having the complement to the DNA taggant will hybridize and generate a detection signal at the unique location of the complementary probe.

Alternatively, if the complementary probe is present in several cells of wells arranged in a particular pattern, then hybridization with the complementary DNA taggant sequence will be detected in the precise pattern of the specific probes in the array or matrix. For example, in the PCR identification method, the nucleic acid taggants, e.g., DNA taggants recovered from the object are amplified by polymerase chain reaction (PCR) and resolved by gel electrophoresis. Since the sequence of the nucleic acid taggants of the present invention are unique and specific to the tagged object, the original nucleic acid will be amplified only by use of primers having specific sequences complementary to a portion of the unique taggant sequence. Through this procedure, if the examined object carries the original nucleic acid, the PCR procedure will amplify extracted nucleic acid to produce amplicons of a predetermined size and a sequence identical to a portion of the original nucleic acid sequence of the taggant. In contrast, if the sample recovered from the examined object does not include the unique nucleic acid corresponding to the authentic object, there will likely be no amplified nucleic acid product, or if the primers do amplify the recovered nucleic acid to produce one or more random amplicons, these one or more amplicons cannot have the unique taggant nucleic acid sequence from the authentic object. Furthermore, the random amplicons derived from counterfeit articles are also of random lengths and the likelihood of producing amplicons of the exact lengths specified by the taggant-specific primers is vanishingly small. Therefore, by comparing the sizes of PCR products, the authenticity of labeled objects can be verified, non-authentic objects can be screened and rejected and anti-counterfeit screening purpose is then achieved.

The number of amplicons amplified and the lengths of the amplicons can be determined after any molecular weight or physical dimension-based separation, such as for instance and without limitation, gel electrophoresis in any suitable matrix medium for example in agarose gels, polyacrylamide gels or mixed agarose-polyacrylamide gels and the electrophoretic separation can be in a slab gel or by capillary electrophoresis.

Alternatively, the deoxyribonucleic acid that has been exposed to alkaline conditions that has been bound to the item or surface of interest can be subjected to PCR, the PCR amplicons can be recovered and sequenced according to well known routine nucleic acid sequencing techniques.

Exemplary embodiments provide methods for increasing the recoverability of a taggant from an object without disturbing the appearance of the object. Several exemplary embodiments of the present invention are described in detail below.

Exemplary embodiments of the present invention also provide methods for authenticating an object using taggants. For example, an exemplary embodiment of the invention provides a method for increasing the recoverability of a taggant from an object; the method includes incorporating a taggant into a solvent, mixing the solution including the taggant with a perturbant to form a first perturbant taggant solution, mixing the first perturbant taggant solution with a polymer to form a second taggant solution and applying the second taggant solution to at least a portion of the object to form a taggant-coated portion of the object. The taggant can be soluble in an aqueous solution. Examples of an aqueous soluble taggant include nucleic acids, saccharides, peptides and many proteins. Alternatively, the taggant can be insoluble in an aqueous solution, or an organic solvent. Examples of a taggant that is insoluble in aqueous solutions or organic solvents include particulate taggants, such as for instance, a up-converting phosphor (UCP) taggant, which may be any suitable UCP taggant, such as a nucleic acid-linked UCP.

An exemplary embodiment of the invention further provides a method for increasing the recoverability of a taggant from an object; the method includes incorporating a taggant in an solution, mixing the solution including the taggant with a perturbant to form a first perturbant taggant solution, mixing the first perturbant taggant solution with a polymer to form a second taggant solution and applying the second taggant solution to at least a portion of the object to form a taggant-coated portion of the object. The solution into which the taggant is incorporated can be an aqueous solution or an organic solvent.

The polymer useful as coatings in the practice of the present invention for incorporating recoverable taggants into coatings of objects of interest can be any polymer that can be used to form a coating on an object, such as for example, epoxy-acrylate, epoxy-urethane, polycarbonate (PC), polymethyl methacrylate (PMMA), polyurethane (PU), polystyrene (PS), polyamides (e.g. nylon 6, nylon 66), polypropylene (PP), polyvinyl chloride (PVC), polysulphones, polyvinylacetate (PVA), polyester (PES), polyethylene terephthalate (PET), polyethylene (PE), benzocyclobutene (BCB), high-density polyethylene (HDPE), polyvinylidene chloride (PVDC), low-density polyethylene (LDPE), high impact polystyrene (HIPS), acrylonitrile butadiene styrene (ABS), phenolics (PF), melamine formaldehyde (MF), polyetheretherketone (PEEK), polyamides, polyetherimide (PEI), polyimide, polyether imide, polyether ketone imide, polylactic acid (PLA), polytetrafluoroethylene (PTFE), polymethyl pentene, polyether ketone, polyether, sulphone (PES), polyphenylene sulfide, polytetrafluoroethylene, butyl rubber, fluropolymers, silicones, Ionomers, moldable elastomers, ethylene vinyl alcohol (EVOH), metalocene polymers and polyethylene naphthalate.

In addition, other polymers into which a taggant can be incorporated according to the methods of the present invention and which can also be used for coating all or part of the surface of an object include, for example, acrylic compounds such as polymethyl methacrylate (PMMA), a transparent thermoplastic synthetic polymer of methyl methacrylate, also called acrylic glass; and acrylic copolymers such as polymethyl methacrylate-polyacrylonitrile copolymers; and the thermosetting epoxy-based polymer compounds such as epoxy-copolymers formed by polymerization of a resin compound and a hardener or activator. The resin is a monomer or short chain having an epoxy group at each terminus. For example a commonly used epoxy resin is formed by a reaction between a reactive epoxide such as epichlorohydrin (a.k.a. glycidyl chloride and 1-chloro-2,3-epoxypropane) and a reactive aromatic compound, such as bisphenol-A. An example of a commonly used hardener is triethylenetetramine (TETA), although almost any polyamine can be substituted. Alternatively, a mixture of two or more of any of the foregoing acrylic compounds and epoxy-based compounds can be used for the coating according to an embodiment of the present invention.

In another exemplary embodiment, the epoxy-based compound that includes the taggant of the present invention can include compounds and resins having two or more epoxy groups. These compounds may be in liquid, gel-like or in solid form. For example, epoxy-based compounds useful in the practice of the present invention include epoxy resins such as: glycidyl ethers obtained by reacting epichlorohydrin with a polyhydric phenol such as bisphenol A, bisphenol F, bisphenol S, hexahydrobisphenol A, tetramethylbisphenol A, diallyl-bisphenol A, hydroquinone, catechol, resorcin, cresol, tetrabromobisphenol A, trihydroxybiphenyl, benzophenone, bisresorcinol, bisphenol hexafluoroacetone, tetramethylbisphenol A, tetramethylbisphenol F, tris(hydroxyphenyl) methane, bixylenol, phenol-novolac, or cresol-novolac; polyglycidyl ethers obtained by reacting epichlorohydrin with an aliphatic polyhydric alcohol such as glycerin, neopentyl glycol, ethylene glycol, propylene glycol, butylene glycol, hexylene glycol, polyethylene glycol, or polypropylene glycol; glycidyl ether esters obtained by reacting epichlorohydrin with a hydroxycarboxylic acid such as p-hydroxybenzoic acid or β-hydroxynaphthoic acid; polyglycidyl esters obtained from polycarboxylic acids such as phthalic acid, methylphthalic acid, isophthalic acid, terephthalic acid, tetrahydrophthalic acid, hexahydrophthalic acid, endomethylene tetrahydrophthalic acid, endomethylene hexahydrophthalic acid, trimellitic acid, and polymerized fatty acids; glycidylamino-glycidyl ethers obtained from aminophenols and aminoalkylphenols; glycidylamino-glycidyl esters obtained from aminobenzoic acids; glycidylamines obtained from aniline, toluidine, tribromoaniline, xylylenediamine, diamino cyclohexane, bisaminomethyl-cyclohexane, 4,4'-diaminodiphenyl methane, and 4,4'-diaminodiphenyl sulfone; and epoxydized polyolefins.

In an exemplary embodiment, the acrylic compound of the polymer for incorporation of the taggant according to the present invention can be, for example, an acrylate compound, an acrylate polymer, an acrylic fiber, an acrylic paint, an acrylic resin, an acrylic glass, or the like.

In an exemplary embodiment of the present invention, the polymer is for example, a natural polymer, a varnish, a polyurethane, a shellac or a lacquer. The varnish, polyurethane, shellac or lacquer can be any suitable varnish, polyurethane, shellac or lacquer, such as for instance and without limitation, a polyurethane varnish from Minwax® Co., Upper Saddle River, N.J. Alternatively the polymer useful as a coating can be a natural polymer, such as beeswax, e.g. the beeswax available from Mountain Rose Herbs, Eugene, Oreg.

In another exemplary embodiment, the polymer is a component of a polymer-containing composition, such as for example, a printing ink. For example, in an exemplary embodiment, the ink may be a heat-curing epoxy-acrylate ink, such as Product No. 4408R or the 970 series Touch Dry® pellet each from Markem®, Keene, N.H. Alternatively, the Artistri® P5000+Series-Pigment Ink sold by Dupont®' or an Epoxy Acrylate Ink, such as Product No. 00-988, Rahn USA Corp. can be used.

The taggants of the present invention include, for example, nucleic acid taggants. Nucleic acid is a general term for deoxyribonucleic acid (DNA) or ribonucleic acid (RNA), and can be synthetic, or derived from an animal, a plant, a bacterium, a virus, a fungus, or a synthetic vector or a fragment of any of the above-listed nucleic acids, etc. It should be noted that a synthetic nucleic acid can have a sequence of a naturally occurring nucleic acid of an animal, plant, bacterium, fungus, virus or any other organism or synthetic vector. Alternatively, a synthetic nucleic acid can have a unique sequence not found in nature. It should be understood that such unique non-natural sequences may have stretches of sequences which are found in nature, but the entire non-natural sequence is unique and is not found in any plant, animal or virus or any other natural organism. In particular, the nucleic acid sequence encoding the element of data or indicia encrypted or encoded in the taggant of the invention is a unique, non-natural sequence and thereby is adapted for use in authentication of an object of interest.

The taggant useful in the practice of the present invention can be any suitable detectable or traceable taggant, for example, a chemical marker or a biological marker. In an embodiment of the methods of the present invention, the taggant is selected from a UV fluorophore, a ceramic IR marker, DNA, an amino acid, a peptide, a protein, a lipid, a sugar, a polysaccharide, a pheromone, a scent, a trace element, a rare earth element, or a combination of any two or more thereof.

In an embodiment of the present invention, the taggant includes a nucleic acid. In one embodiment, the taggant consists essentially of DNA and no other significant component useful for identification or authentication.

In addition, other taggants such as, for example, ultraviolet (UV) taggants, Up Converting Phosphor (UCP) infrared (IR) taggants, UV marker taggants, UV fluorophore taggants, ceramic IR marker taggants, protein taggants, and/or trace element taggants can be used in combination with nucleic acid taggants. In an exemplary embodiment, the taggants used may include, for example, a combination of DNA taggants, and an IR upconverting phosphor (UCP) taggant. Alternatively, in another exemplary embodiment, the taggants used may include, for example, a combination of DNA taggants, an IR upconverting phosphor (UCP) taggant and a UV taggant. For example, in an exemplary embodiment, the IR (UCP) taggant can be, for example, a green, a blue or a red (UCP) IR taggant, such as for instance the Green IR Marker, Product No. BPP-1069; the Blue UCP, Product No. BPP-1070; or the Red UCP, Product No. BPP-1071 from Boston Applied Technologies Inc., Woburn, Mass.

The solution in which the soluble taggants are dissolved according to the methods of the present invention can include, for example, water, TE buffer (10 mM Tris.HCl, 1 mM EDTA), Tris-glycine buffer, Tris-NaCl buffer, TBE buffer (Tris-borate-EDTA), TAE buffer (Tris-acetate-EDTA) and TBS buffer (Tris-buffered saline), HEPES buffer (N-(2-Hydroxyethyl)piperazine-N'-ethanesulfonic acid), MOPS buffer (3-(N-Morpholino)propanesulfonic acid), PIPES buffer (Piperazine-N,N'-bis(2-ethanesulfonic acid), MES buffer (2-(N-Morpholino)ethanesulfonic acid), PBS (Phosphate Buffered Saline), PBP buffer (sodium phosphate+ EDTA), TEN buffer (Tris/EDTA/NaCl), TBST buffer (Tris-HCl, NaCl, and Tween 20), PBST buffer (Phosphate Buffered Saline with Tween 20) and any of the many other known buffers used in the biological and chemical sciences.

In an exemplary embodiment the perturbant useful for the practice of the present invention can be any suitable perturbant, such as a polyol or a diol or glycol, a starch or a pyrrolidone. The polyol can be any suitable polyol, such as a polyethylene glycol polymer, for instance a PEG 200 i.e. a polyethylene glycol having an average molecular number of 200 ethylene glycol units per chain (such as the PEG200 $M_n$ 200 Product No. P3015), Sigma-Aldrich, St. Louis, Mo. Alternatively, in another embodiment, the polyethylene glycol can be a PEG 10,000 polyol polymer such as the PEG10, 000 Product No. P3015, $M_n$ 10,000 from Sigma-Aldrich.

In another embodiment, the glycol useful as a perturbant according to the invention can be any suitable glycol or diol, such as for instance, ethylene glycol, diethylene glycol, glycerol, methanediol, triethylene glycol, propylene glycol from Sigma-Aldrich, or 1,2-butanediol or 1,4-from butanediol from Fluka Analytical.

In another embodiment, the starch can be for example a hydroxylpropyl starch such as Zeina® B860 from Grain Processing Corp., Muscatine, Iowa. In still another embodiment, the pyrrolidone perturbant of the invention can be any suitable pyrrolidone such as for instance an N-alkyl pyrrolidone, or the caprylyl pyrrolidone surfactant: Surfadone® LP100 available from Ashland Inc., Covington, Ky.

In an exemplary embodiment, the perturbant of the present invention can be used in a solution containing the polymer and the taggant in an amount of about 0.1 to about 30% w/w of the taggant in the solution. In another exemplary embodiment, the perturbant of the present invention can be used in a solution containing the polymer and the taggant in an amount of about 1% to about 25% w/w of the taggant in the solution. Alternatively, the perturbant of the present invention can be used in a solution containing the polymer and the taggant in an amount of about 5% to about 20% w/w of the taggant in the solution.

In another exemplary embodiment, the perturbant of the present invention can be used in a solution containing the polymer and the taggant in an amount of about 7% to about 15% w/w of the taggant in the solution. In still another exemplary embodiment, the perturbant of the present invention can be used in a solution containing the polymer and the taggant in an amount of about %10 w/w of the taggant in the solution.

Alternatively, in one exemplary embodiment, the perturbant of the present invention can be used in a solution containing the polymer and the taggant in an amount of about 0.1% to about 30% w/w of the taggant in the solution. In another exemplary embodiment, the perturbant of the present invention can be used in a solution containing the polymer and the taggant in an amount of about 5% to about 30% w/w of the taggant in the solution. Alternatively, the perturbant of the present invention can be used in a solution containing the polymer and the taggant in an amount of about 10% to about 30% w/w of the taggant in the solution.

In one exemplary embodiment, the perturbant of the present invention can be used in a solution containing the polymer and the taggant in an amount of about 1% to about 25% w/w of the taggant in the solution. In an exemplary embodiment, the perturbant of the present invention can be used in a solution containing the polymer and the taggant in an amount of about 1% to about 20% w/w of the taggant in the solution. In an exemplary embodiment, the perturbant of the present invention can be used in a solution containing the polymer and the taggant in an amount of about 1% to about 15% w/w of the taggant in the solution. In an exemplary embodiment, the perturbant of the present invention can be used in a solution containing the polymer and the taggant in an amount of about 1% to about 10% w/w of the taggant in the solution.

Without wishing to be bound by theory, it is believed that the perturbants of the present invention create microcrevices and micropockets and microenvironments in the polymerized polymer facilitating recovery of the taggant (e.g. a DNA taggant) more efficiently than from polymerized coatings lacking such perturbants.

The objects of interest coated with the taggants according to exemplary embodiments of the present invention include, for example, ceramic surfaces, plastic films, vinyl sheets, antiques, items of jewelry, identification cards, credit cards, magnetic strip cards, paintings, artwork, souvenirs, sports collectibles and other collectibles. The authenticity of these objects can then be verified by recovering and identifying the taggants coated thereon through, for example, methods described in further detail below.

The coating that includes or incorporates a taggant of the invention which can be applied to an object of interest can be any suitable coating which is stable and capable of incorporating the taggant, for example, a plastic, a varnish, a polyurethane, a shellac or a lacquer. Alternatively, the coating can be beeswax.

Alternatively, the coating of the present invention applied to an object of interest can be, for example, an ink, a paint, a sealer, a glue, a coating containing one or more dyes, one or more dyestuffs, or one or more pigments, and other such common coatings.

In another embodiment of the present invention, the method comprises incorporating or dissolving the taggant in a solution to form a taggant solution prior to mixing the nucleic acid taggant with the perturbant, mixing the first solution with a polymer to form a second solution, and applying the second solution to at least a portion of the object to form a taggant-coated portion of the object, wherein the taggant is recoverable from the object.

In one embodiment, the second solvent, is a non-polar solvent. In one embodiment, the second solvent is selected from the group consisting of methyl ethyl ketone (MEK), acetone, an alcohol, such as for instance methanol, ethanol, n-propanol, isopropanol, n-butanol, or isobutanol etc. or an ether, such as for instance dimethylether, methylethyl ether and diethyl ether etc. Alternatively, the second solvent can be a combination of two or more ketones, alcohols, or ethers. In another alternative the second solvent can be a combination of any two or more of the above solvents.

In another embodiment, the taggant includes an IR upconverting phosphor (UCP) taggant and a DNA taggant, and wherein the perturbant is a polyol.

In still another embodiment, the polymer is a varnish, a polyurethane, a shellac or a lacquer.

In one embodiment of the present invention, the solution enhancer includes at least one polyol. The polyol can be any suitable polyol, such as for ethylene glycol, diethylene glycol, glycerol, methanediol, 1,2-butanediol, 1,4-butanediol, triethylene glycol, propylene glycol, and polyethylene glycol (PEG). The polyethylene glycol can be of any suitable size, such as for instance and without limitation, PEG 200, PEG 400, PEG 600, PEG 2000, PEG 3350 or PEG 10,000.

For example, the polyethylene glycol may be any suitable polyethylene glycol available from Sigma-Aldrich, St. Louis, Mo. The PEG200 may be, for example $M_n$ 200, Product No. P3015. The PEG 400 may be, for example, $M_n$ 400, Product No. 202398. The PEG600 may be, for example, $M_n$ 600 waxy moist solid, Product No. 202401. The PEG2,000 may be, for example, $M_n$ 1900-2200 solid flakes, Product No. 295906-250G. The PEG3350 may be, for example, $M_n$ 3000-3700, Product No. 83272. In another exemplary embodiment, the PEG10,000 may be, for example, $M_n$ 10,000, Product No. 309028.

In another embodiment, the polymer is selected from the group consisting of polycarbonate (PC), polymethyl methacrylate (PMMA), polyurethane (PU), polystyrene (PS), nylon or polypropylene (PP) all of which are readily commercially available. In another embodiment, the polymer includes a first solvent comprising a polymeric compound the polymerization of which can be initiated and hardened by heat, UV or a catalyst.

In one embodiment, the method of the present invention further includes curing or drying the second solution applied on the object to provide a coating including the taggant. The coating can be over all or part of the object to be identified, validated, authenticated, or tracked.

After coating an object with the taggant-containing polymer according to the methods of the present invention, the coating can be, dried or cured such that the coating adheres to the object, thereby providing the object with authentication, tracking and anti-counterfeiting functions.

In exemplary embodiments of the present invention, the taggant can be recovered from the taggant-coated portion of the object without disturbing the appearance of the object. For example, the taggant can be recovered from the taggant-coated portion of the object by swabbing a surface of the object. In one exemplary embodiment, the object may be swabbed with a cotton swab, a cotton ball, a cotton fabric, a filter or a tissue paper, or any other suitable sampling medium. For example, in an exemplary embodiment the taggant is recovered from the taggant-coated portion of the object using any suitable solvent on an applicator such as a cotton-tipped applicator. The solvent can be any suitable solvent available from reagent vendors such as Sigma-Aldrich. Suitable solvents include, for instance, ethanol, methanol, propanol, toluene, xylene and methylethylketone (MEK, 2-butanone), to name but a few. Other suitable commonly available solvents will be readily identifiable by those of skill in the art.

In an embodiment of the invention, the polymer into which the polymer into which the first solution containing the solution enhancer and taggant is mixed, can be gasoline, diesel fuel, such as the gasoline or diesel fuel, a lubricant oil such as motor oil, heating oil, kerosene, jet fuel or unrefined crude oil, and the like.

Exemplary embodiments of the present invention also provide a method for authenticating an object which includes providing an object comprising a coating comprising a taggant, a perturbant and a polymer, recovering the taggant from the object for identification, tracking, or verifying the authenticity of the object by identifying the unique taggant. In one embodiment, the unique taggant is a DNA taggant having a unique DNA sequence and the unique non-natural DNA sequence is stored in a database that matches the unique DNA sequence to the data elements corresponding to the object which is coated with the unique taggant. The database can in turn be located on a computer that can be accessed in order to locate, track, authenticate and verify the identity of the tagged object from which the taggant was recovered.

DNA taggants useful in the examples described below include any suitable DNA taggant, such as for instance, in one embodiment, the DNA taggant is a double stranded DNA oligomer having a length of between about 40 base pairs and about 1000 base pairs. In other embodiments the DNA taggant is a double stranded DNA oligomer with a length of between about 80 and 500 base pairs. In another embodiment the DNA taggant is a double stranded DNA oligomer having a length of between about 100 and about 250 base pairs.

Alternatively, the DNA taggant can be single-stranded DNA or any suitable length, such as between about 40 bases and about 1000 bases; between about 80 and 500 bases; or between about 100 and about 250 bases. The DNA taggant can be natural DNA, whether isolated from natural sources or synthetic; or the DNA taggant can be a synthetically produced non-natural sequence. All or a portion of the DNA may comprise an identifiable sequence.

In one exemplary embodiment, the DNA taggant is identifiable by any suitable detection and/or identification method such as for example, hybridization with a taggant-sequence specific nucleic acid probe, an in situ hybridization method (including fluorescence in situ hybridization: FISH), amplification using a polymerase chain reaction (PCR), such as quantitative/real time PCR and detection of the amplified sequences (amplicons) by any of the variety of standard well known methods.

For example, in the PCR identification method, the nucleic acid taggants, e.g., DNA taggants recovered from the object are amplified by polymerase chain reaction (PCR) and resolved by gel electrophoresis. Since the sequence of the nucleic acid taggants of the present invention are unique and specific to the tagged object, the original nucleic acid will be amplified only by use of primers having specific sequences complementary to a portion of the unique taggant sequence. Through this procedure, if the examined object carries the original nucleic acid, the PCR procedure will amplify extracted nucleic acid to produce amplicons of a predetermined size and a sequence identical to a portion of the original nucleic acid sequence of the taggant.

In contrast, if the sample recovered from the examined object does not include the unique nucleic acid corresponding to the authentic object, there will likely be no amplified nucleic acid product, or if the primers do amplify the recovered nucleic acid to produce one or more random amplicons, these one or more amplicons cannot have the unique taggant nucleic acid sequence from the authentic object. Furthermore, the random amplicons derived from counterfeit articles are also of random lengths and the likelihood of producing amplicons of the exact lengths specified by the taggant-specific primers is vanishingly small. Therefore, by comparing the sizes of PCR products, the authenticity of labeled objects can be verified, non-authentic objects can be screened and rejected and anti-counterfeit screening purpose is then achieved.

The number of amplicons amplified and the lengths of the amplicons can be determined after any molecular weight or physical dimension-based separation, such as for instance and without limitation, gel electrophoresis in any suitable matrix medium for example in agarose gels, polyacrylamide gels or mixed agarose-polyacrylamide gels and the electrophoretic separation can be in a slab gel or by capillary electrophoresis.

Compounds Utilized in the Methods of the Invention

The methods of authentication of an item of the invention comprise compounds of the formula I:

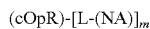

wherein:
  m is an integer greater than 1;
  (cOpR) is a coated optical reporter particle;
  (NA) is a nucleic acid oligomer of detectable sequence; and
  L is a linking group covalently bound to the coated optical reporter particle and to the nucleic acid oligomer.

While formula I specifically relates to linking nucleic acid oligomers or nucleotides to the surface of the coated optical reporter particle, it should be understood to the those skilled in the art that other biomolecules besides nucleotides can be covalently linked to L. Such biomolecules include but are not limited to peptides, proteins, antibodies, enzymes, DNA binding proteins and the like. These biomolecules, maybe modified to include lipids, carbohydrates, fluorescent and/or upconverting phosphor molecules or other detectable compounds or markers.

In many embodiments, NA is a DNA oligomer. The DNA oligomer maybe either single stranded DNA or double stranded DNA. In certain embodiments NA maybe comprise cDNA, RNA, STR (single tandem repeat) or SNP (single nucleotide polymorphism). NA oligomers of the compositions of the invention may also be modified to comprise at least one dUTP nucleic acid or at least one nucleic acid within the oligomer which has been modified to contain a detectable marker.

In many embodiments NA is a DNA oligomer having a length of between about 40 base pairs and about 1000 base pairs (per strand).

In other embodiments the DNA has a length of between about 80 and 500 base pairs (per strand).

In yet other embodiments the DNA has a length of between about 100 to about 250 base pairs (per strand).

The DNA used with the invention maybe natural or synthetically produced. All or a portion of the DNA may comprise an identifiable sequence encoded in a single-stranded, double-stranded, linear or circular DNA molecule; or in an RNA (ribonucleic acid) molecule.

In certain embodiments of formula I, the coated optical reporter comprises a visible or infrared detectable light emitting material selected from the group consisting of a fluorescent dye, an upconverting phosphor (comprising a coupled pair of rare-earth atoms capable of combining the energy of two or more photons to emit a higher energy emission photon of a precise wavelength for detection and identification), a ceramic powder, or a quantum dot material. In most embodiments where the cOpR comprises a visible or infrared detectable light emitting material, the light emitting materials are excitable by UV, visible or an infrared light source.

In some embodiments, rare earth-doped ceramic particles are used as phosphor particles. Phosphor particles may be detected by any suitable method, including but not limited to up-converting phosphor technology (UPT), in which up-converting phosphors transfer lower energy infrared (IR) radiation into higher-energy visible light. Although an understanding of the mechanism is not necessary to practice the present invention and the present invention is not limited to any particular mechanism of action, in some embodiments the UPT up-converts infrared light to visible light by multi-photon absorption and subsequent emission of dopant-dependant phosphorescence (See, e.g., U.S. Pat. No. 6,399,397; van De Rijke, et al., Nature Biotechnol. 19(3):273-6 (2001); Corstjens, et al., IEE Proc. Nanobiotechnol. 152(2):64 (2005).

Incorporation of the Nucleic Acid Tag into an Item of Interest

Methods useful for incorporating DNA into the materials of articles, or coating articles with optical reporters and DNA are described in US Patent Application publication No. 2008-0299559 of Kwok et al. Methods useful for incorporating DNA into, or coating onto articles with optical reporters and DNA into inks for secure document printing and detection useful in the practice of the present invention are described in US 2009-0042191. Methods useful for incorporating DNA into indicia, or coating of indicia, such as sports goods, logos or badges with optical reporters and DNA are described in US Patent Application publication No. US 2008-0293052. Methods useful for incorporating DNA into, or coating onto pharmaceutical compositions, such as tablets useful in the practice of the present invention are described in US Patent Application publication No. 2009-0075261.

The method of incorporating the nucleic acid tag into an item of interest depends significantly on the type of product to be authenticated as described above. The nucleic acid tag maybe added to a marker compound in a "naked" or encapsulated form at a predetermine concentration which allows for accurate detection of the nucleic acid taggant. The marker compound is generally a liquid but in certain embodiments is a solid. The marker compound maybe a liquid and after the addition of the nucleic acid taggant, is dried prior to introducing the marker as an inert substance of a particular product. When the marker compound comprising a nucleic acid taggant is in liquid form, the marker compound is generally applied to the product in a lacquer, paint or liquid aerosol form.

In other embodiments the nucleic acid taggant may be applied to the finished document as a paint/ink on a pre-designated position on the document. The ink utilized is formulated to allow detection of an up converting phosphor particle, with minimal quenching of the light emission from the UCP when excited by the appropriate light source.

When the document is a painting, for example, the nucleic acid taggant can be mixed with paints appropriate for the type of painting being marked. The NA taggant is added to the paint mixture at an appropriate concentration to allow for adequate detection of the NA marker. If the NA taggant marker comprises an UCP composition, the paint mixture is compatible with the NA taggant as to not quench the emission of the UCP particle. In some instances, the NA taggant marker may be introduced to the painting as a topcoat or varnish as a topical application on the painting.

Nucleic Acid Tag Extraction and Capture Methods

A variety of nucleic acid extraction solutions have been developed over the years for extracting nucleic acid sequences from a sample of interest. See, for example, Sambrook et al. (Eds.) Molecular Cloning, (1989) Cold Spring Harbor Press. Many such methods typically require one or more steps of, for example, a detergent-mediated step, a protease treatment step, a phenol and/or chloroform extraction step, and/or an alcohol precipitation step. Some nucleic acid extraction solutions may comprise an ethylene glycol-type reagent or an ethylene glycol derivative to increase the efficiency of nucleic acid extraction while other methods only use grinding and/or boiling the sample in water. Other methods, including solvent-based systems and sonication, could also be utilized in conjunction with other extraction methods.

In some embodiments, the authentication process comprises capturing the nucleic acid tag directly with a complementary hybridization probe attached to a solid support. In general, the methods for capturing the nucleic acid tag involve a material in a solid-phase interacting with reagents in the liquid phase. In certain aspects, the nucleic acid probe is attached to the solid phase. The nucleic acid probe can be in the solid phase such as immobilized on a solid support, through any one of a variety of well-known covalent linkages or non-covalent interactions. In certain aspects, the support is comprised of insoluble materials, such as controlled pore glass, a glass plate or slide, polystyrene, acrylamide gel and activated dextran. In other aspects, the support has a rigid or semi-rigid character, and can be any shape, e.g. spherical, as in beads, rectangular, irregular particles, gels, microspheres, or substantially flat support. In some embodiments, it can be desirable to create an array of physically separate sequencing regions on the support with, for example, wells, raised regions, dimples, pins, trenches, rods, pins, inner or outer walls of cylinders, and the like. Other suitable support materials include, but are not limited to, agarose, polyacrylamide, polystyrene, polyacrylate, hydroxethylmethacrylate, polyamide, polyethylene, polyethyleneoxy, or copolymers and grafts of such. Other embodiments of solid-supports include small particles, non-porous surfaces, addressable arrays, vectors, plasmids, or polynucleotide-immobilizing media.

As used in the methods of capturing the nucleic acid tag, a nucleic acid probe can be attached to the solid support by covalent bonds, or other affinity interactions, to chemically reactive functionality on the solid-supports. The nucleic acid can be attached to solid-supports at their 3',5', sugar, or nucleobase sites. In certain embodiments, the 3' site for attachment via a linker to the support is preferred due to the many options available for stable or selectively cleavable linkers. Immobilization is preferably accomplished by a covalent linkage between the support and the nucleic acid. The linkage unit, or linker, is designed to be stable and facilitate accessibility of the immobilized nucleic acid to its sequence complement. Alternatively, non-covalent linkages such as between biotin and avidin or streptavidin are useful. Examples of other functional group linkers include ester, amide, carbamate, urea, sulfonate, ether, and thioester. A 5' or 3' biotinylated nucleotide can be immobilized on avidin or streptavidin bound to a support such as glass.

Depending on the initial concentration of the nucleic acid tag added to the product of interest, the tag can be detected quantitatively without being amplified by PCR. In some embodiments, a single stranded DNA tag labeled with a detection molecule (i.e. fluorophore, biotin, etc.) can be hybridized to a complementary probe attached to a solid support to allow for the specific detection of the "detection molecule" configured to the tag. The nucleic acid DNA tag can also be double stranded, with at least one strand being labeled with a detection molecule. With a dsDNA tag, the nucleic acid tag must be heated sufficiently and then quick cooled to produce single stranded DNA, where at least one of the strands configured with a detection molecule is capable of hybridizing to the complementary DNA probe under appropriate hybridization conditions.

In certain aspects of the invention, the complementary probe is labeled with a detection molecule and allowed to hybridize to a strand of the nucleic acid tag. The hybridization of the probe can be completed within the product, when the product is a textile or can be completed after the nucleic acid tag/marker has been extracted from the product, such as when the products are liquid (e.g. oil, gasoline, perfume, etc.). The direct detection methods described herein depend on having a large initial concentration of nucleic acid label embedded into the product or rigorous extraction/capture methods which concentrate the nucleic acid tag extracted from a large volume or mass of a particular product.

In one embodiment, where the NA taggant comprises an up converting particle, the extraction of the NA taggant marker varies depending on if the document being authenticated. when the NA marker comprises a UCP particle, the NA marker can be located by detecting the presence of the UCP by an appropriate light source. The NA marker can then be extracted from the document by scraping, cutting out, or dissolving the portion of the document which is determined to have the presence of the correct up-converting phosphor particle(s). Once the portion of the item containing the NA marker has been removed the item of interest, the NA marker may isolated and/or prepared for PCR analysis utilizing techniques known to those skilled in the art of PCR sample preparation.

Real-Time PCR Amplification

In many embodiments, the authentication process comprises amplifying the nucleic tag by polymerase chain reaction. However, conventional PCR amplification is not a quantitative detection method. During amplification, primer dimers and other extraneous nucleic acids are amplified together with the nucleic acid corresponding to the analyte. These impurities must be separated, usually with gel separation techniques, from the amplified product resulting in possible losses of material. Although methods are known in which the PCR product is measured in the log phase, these methods require that each sample have equal input amounts of nucleic acid and that each sample amplifies with identical efficiency, and are therefore, not suitable for routine sample analyses. To allow an amount of PCR product to form which is sufficient for later analysis and to avoid the difficulties noted above, quantitative competitive PCR amplification uses an internal control competitor and is stopped only after the log phase of product formation has been completed.

In a further development of PCR technology, real time quantitative PCR has been applied to nucleic acid analytes or templates. In this method, PCR is used to amplify DNA in a sample in the presence of a nonextendable dual labeled fluorogenic hybridization probe. One fluorescent dye serves as a reporter and its emission spectra is quenched by the second fluorescent dye. The method uses the 5' nuclease activity of Taq polymerase to cleave a hybridization probe during the extension phase of PCR. The nuclease degradation of the hybridization probe releases the quenching of the reporter dye resulting in an increase in peak emission from the reporter. The reactions are monitored in real time. Reverse transcriptase (RT)-real time PCR (RT-PCR) has also been described (Gibson et al., 1996). Numerous commercially thermal cyclers are available that can monitor fluorescent spectra of multiple samples continuously in the PCR reaction, therefore the accumulation of PCR product can be monitored in 'real time' without the risk of amplicon contamination of the laboratory. Heid, C. A.; Stevens, J.; Livak, K. L.; Williams, P. W. (1996). Real time quantitative PCR. Gen. Meth. 6: 986-994. Real time PCR, Saunders & Lee, July 2013, Calister Academic Press.

In some embodiments of the anti-counterfeit authentication process, real time PCR detection strategies may be used, including known techniques such as intercalating dyes (ethidium bromide) and other double stranded DNA binding dyes used for detection (e.g. SYBR green, a highly sensitive fluorescent stain, FMC Bioproducts), dual fluorescent probes (Wittwer, C. et al., (1997) BioTechniques 22: 176-181) and panhandle fluorescent probes (i.e. molecular beacons; Tyagi S., and Kramer F R. (1996) Nature Biotechnology 14: 303-308). Although intercalating dyes and double stranded DNA binding dyes permit quantitation of PCR product accumulation in real time applications, they suffer from the previously mentioned lack of specificity, detecting primer dimer and any non-specific amplification product. Careful sample preparation and handling, as well as careful primer design, using known techniques must be practiced to minimize the presence of matrix and contaminant DNA and to prevent primer dimer formation. Appropriate PCR instrument analysis software and melting temperature analysis permit a means to extract specificity and may be used with these embodiments.

PCR amplification is performed in the presence of a non-primer detectable probe which specifically binds the PCR amplification product, i.e., the amplified detector DNA moiety. PCR primers are designed according to known criteria and PCR may be conducted in commercially available instruments. The probe is preferably a DNA oligonucleotide specifically designed to bind to the amplified detector molecule. The probe preferably has a 5' reporter dye and a downstream 3' quencher dye covalently bonded to the probe which allow fluorescent resonance energy transfer. Suitable fluorescent reporter dyes include 6-carboxy-fluorescein (FAM), tetrachloro-6-carboxy-fluorescein (TET), 2,7-dimethoxy-4,5-dichloro-6-carboxy-fluorescein (JOE) and hexachloro-6-carboxy-fluorescein (HEX). A suitable reporter dye is 6-carboxy-tetramethyl-rhodamine (TAMRA). These dyes are commercially available from Perkin-Elmer, Philadelphia, Pa. Detection of the PCR amplification product may occur at each PCR amplification cycle. At any given cycle during the PCR amplification, the amount of PCR product is proportional to the initial number of template copies. The number of template copies is detectable by fluorescence of the reporter dye. When the probe is intact, the reporter dye is in proximity to the quencher dye which suppresses the reporter fluorescence. During PCR, the DNA polymerase cleaves the probe in the 5'-3' direction separating the reporter dye from the quencher dye increasing the fluorescence of the reporter dye which is no longer in proximity to the quencher dye. The increase in fluorescence is measured and is directly proportional to the amplification during PCR. This detection system is now commercially available as the TaqMan PCR system from Perkin-Elmer, which allows real time PCR detection.

In an alternative embodiment, the reporter dye and quencher dye may be located on two separate probes which hybridize to the amplified PCR detector molecule in adjacent locations sufficiently close to allow the quencher dye to quench the fluorescence signal of the reporter dye. As with the detection system described above, the 5'-3' nuclease activity of the polymerase cleaves the one dye from the probe containing it, separating the reporter dye from the quencher dye located on the adjacent probe preventing quenching of the reporter dye. As in the embodiment described above, detection of the PCR product is by measurement of the increase in fluorescence of the reporter dye.

Molecular beacons systems are frequently used with real time PCR for specifically detecting the nucleic acid template in the sample quantitatively. For instance, the Roche Light Cycler® or other such instruments may be used for this purpose. The detection molecule configured to the molecular beacon probe may be visible under daylight or conventional lighting and/or may be fluorescent. It should also be noted that the detection molecule may be an emitter of radiation, such as a characteristic isotope.

The ability to rapidly and accurately detect and quantify biologically relevant molecules with high sensitivity is a central issue for medical technology, national security, public safety, and civilian and military medical diagnostics. Many of the currently used approaches, including enzyme linked immunosorbant assays (ELISAs) and PCR are highly sensitive. However, the need for PCR amplification makes a detection method more complex, costly and time-consuming. In certain embodiments anti-counterfeit nucleic acid tags are detected by Surface Enhanced Raman Scattering (SERS) as described in U.S. Pat. No. 6,127,120 by Graham et al. SERS is a detection method which is sensitive to relatively low target (nucleic acid) concentrations, which can preferably be carried out directly on an unamplified samples. Nucleic acid tags and/or nucleic acid probes can be labeled or modified to achieve changes in SERS of the nucleic acid tag when the probe is hybridized to the nucleic acid tag. The use of SERS for quantitatively detecting a nucleic acid provides a relatively fast method of analyzing and authenticating a particular product.

Another detection method useful in the invention is the Quencher-Tether-Ligand (QTL) system for a fluorescent biosensor described in U.S. Pat. No. 6,743,640 by Whitten et al. The QTL system provides a simple, rapid and highly-sensitive detection of biological molecules with structural specificity. QTL system provides a chemical moiety formed of a quencher (Q), a tethering element (T), and a ligand (L). The system is able to detect target biological agents in a sample by observing fluorescent changes.

The QTL system can rapidly and accurately detect and quantify target biological molecules in a sample. Suitable examples of ligands that can be used in the polymer-QTL approach include chemical ligands, hormones, antibodies, antibody fragments, oligonucleotides, antigens, polypeptides, glycolipids, proteins, protein fragments, enzymes, peptide nucleic acids and polysaccharides. Examples of quenchers for use in the QTL molecule include methyl viologen, quinones, metal complexes, fluorescent dyes, and electron accepting, electron donating and energy accepting moieties. The tethering element can be, for example, a single bond, a single divalent atom, a divalent chemical moiety, and a multivalent chemical moiety. However, these examples of the ligands, tethering elements, and quenchers that form the QTL molecule are not to be construed as limiting, as other suitable examples would be easily determined by one of skill in the art.

After the nucleic acid fragment/marker compound with a known nucleic acid sequence has been manufactured and applied to the item, the method further comprises generating an item having a DNA fragment marker or tag. The particular product or item generated may be tagged with a nucleic acid marker throughout the complete product or only in a predetermined region of the product. When the product to be authenticated is a solid, a specified amount of nucleic acid marker maybe incorporated throughout the volume of the product, only on the surface of the product or in some embodiments, placed only on a previously designated section of the product.

In one embodiment the item to be tagged is an ink, paint or pigment that may be in liquid, powder or gel form. The nucleic acid marker or taggant may be introduced to the ink at a desired concentration and intermixed with the ink. The ink may be present in a container or cartridge when the nucleic acid marker is added, or the labeled ink may be subsequently transferred into printer cartridges, pens for signing documents, into official stamp ink pads or blotting pads such as utilized by a notary, spray containers, or other containers.

In certain embodiments the item generated is a printed item such as a document or lithographic print. In such embodiments the nucleic acid-labeled ink may be applied to the document by various print transfer techniques, or by brushing, spraying, blotting or other method of applying ink to a document.

If the product is a textile garment, the marker could be either solid or liquid and applied to a predetermined area of the garment. Textiles may have a label with the manufactures name on it and may also be used as a region of the product which the nucleic acid marker is placed. The above examples are presented for clarity and are not meant to be limiting in scope.

In one embodiment, the item to be marked is a thread or textile product. The thread or textile product can be any suitable thread or textile product, such as for instance and without limitation: any natural fiber product, e.g. a cotton fiber product or a wool fiber product. Alternatively, the thread or textile product can be a synthetic thread or fiber product, such as for instance, an extruded fiber, e.g. a reconstituted cellulose thread, a plastic, polyester, or nylon thread or fiber, or fabric woven from such a plastic, polyester, or nylon thread or fiber.

In another embodiment, the item to be marked by the methods of the present invention is a bank note or item of currency, such as a paper currency note or a paper currency note with one or more security components, such as colored cotton fibers or a metal thread or water mark. In some countries blended paper and plastic sheets are used for currency notes. These can also be marked with DNA and optional reporters by methods of the present invention.

In another embodiment, the item to be marked with a DNA marker and reporters by methods of the present invention include specialty building materials. The specialty building material can be any suitable specialty building material such as for instance, antimicrobial drywall sheets suitable for construction in hospitals and clinics and medical facilities.

After the DNA marker has been prepared and associated with an item of interest as described above, the DNA marker may then be detected and a sample of the DNA marker may be collected from the item of interest for authentication as explained below.

Detection Methods

In general, when the taggant is dsDNA, PCR is the technique for taggant detection as described above. The copy number of DNA taggant in a predetermined sample size of marker compound used for authentication is in a range from about 3 copies to about 100,000 copies, more preferably about 10 copies to about 50,000 copies, and even more preferably about 100 copies to about 10,000 copies of DNA taggant. The concentration of NA taggant within the ink or pigment may be varied as required depending upon particular embodiments of the invention. PCR can effectively detect extremely small amounts of DNA taggant and skilled persons can easily formulate DNA-labeled inks using the invention.

An embodiment of the method of authenticating and verifying an item further includes preparing the item to be verified. Next, a sample may be collected of the particular item of interest for verification, i.e., DNA analysis on whether the item contains the nucleotide tag. For example, the preparation may comprise sampling the ink or pigment within a printer cartridge or other container. Where the item prepared is a document or printed item a portion of the document containing NA-tagged ink may be cut, scraped, abraded, tape-pulled or otherwise removed from the document for analysis. Preparation of the document may require cleaning or solvent treatment prior to removing a sample portion of the document to be verified. Preparation of the item may occur without further purification, but usually, some extraction, isolation or purification of the nucleic acid tag obtained in the sample is required. Details on the extraction, concentration and purification techniques useful for the methods of the invention are described in detail above.

In certain embodiments the placement or position of the NA marker on the item of interest may be located by the detection of materials or compounds configured to or associated with the NA fragment in the NA marker. In many embodiments the DNA marker may be bound or coupled to, or otherwise associated with, a chemically or optically detectable label. Detection of DNA-labeled portions of the item may be carried out by optically detecting fluorescent dyes or upconverting phosphor particles which can be detected easily by UV and/or IR portable light sources. Thus, for example, a printed document could be examined with a UV or IR light source to find a particular region or regions of the document that contain a particular fluorescent marker. In this manner, only a small portion of the item (as identified by the fluorescent dye or particles) needs to be sampled for DNA. The materials or compounds utilized for locating the position of the NA marker on a document or item of interest maybe coated with functional groups which can covalently bind to the NA fragment(s) of the NA marker, as described above.

In general, analyzing the item for the presence of DNA, comprises providing a "detection molecule" configured to the nucleic acid tag. A detection molecule includes but is not limited to a nucleic acid probe and/or primer set which is complementary to the sequence of the nucleic acid taggant, or a dye label or color producing molecule configured to bind and adhere to the nucleic acid taggant. When the detection of the nucleic acid taggant comprises amplifying the nucleic acid taggant using PCR, the detection molecule(s) are primers which specifically bind to a certain sequence of the nucleic acid taggant. When real time PCR is utilized in the analysis of the sample, an identifiable nucleotide probe may also be provided to enhance the detection of the nucleic acid taggant as well as provide semi-quantitative or quantitative authentication results. With the use of real time PCR, results from the analysis of the sample can be completed within 30 minutes to 2 hours, including extracting or purifying the nucleic acid taggant from the collected sample. Various embodiments utilize a wide range of detection methods besides for PCR and real time PCR, such as fluorescent probes, probes configured to molecules which allow for the detection of the nucleic acid tag when bound to the probe by Raman spectroscopy, Infrared spectroscopy or other spectroscopic techniques used by those skilled in the art of nucleic acid detection. The method utilized to detect the nucleic acid is dependent on the quantity of nucleic acid taggant associated with the optical reporter marker. When only a few copies of NA taggant are collected in the marker sample, high sensitivity techniques such as PCR may be preferable over fluorescent probes.

The results of the analysis of the ink, ink cartridge, pigment, printed document or other item are reviewed to determine if the specific nucleic acid taggant is present in the sample. If so, the authentication of whether the item is genuine or not can be verified. If the nucleic acid taggant is not found or detected in the item of interest, the conclusion from the analysis is that the item is not authentic or has been tampered with. If the nucleic acid taggant is detected in the item, then the item is verified as being authentic.

The results of the analysis of the collected sample are reviewed and a query or determination is made as to whether or not the specific nucleic acid taggant was detected in the sample. If the nucleic acid taggant is not found or not detected in the collected sample of the item of interest, the conclusion from the analysis is the that item is not authentic or has been tampered with. If the nucleic acid taggant is detected in the sample, then the item is verified as being authentic.

If a determination is that an item is not authentic, a different, earlier point in the supply or commerce chain may be selected and then the steps discussed above of detecting the DNA marker, and the collecting and analyzing a sample may be repeated. Thus an item from an earlier point in the supply chain would be selected, the optical reporter marker detected, and a sample collected and analyzed. If it is again determined that the item is not authentic or has been otherwise tampered with, then the steps discussed above of detecting the DNA marker, and the collecting and analyzing a sample may be repeated with an item selected from yet an earlier point in the supply chain. In this manner, the time and/or location of tampering or counterfeit substitute may be located.

In some embodiments, the quantity or concentration of the nucleic acid taggant within a collected sample can be determined and compared to the initial amount of nucleic acid taggant placed in the product to allow for the detection of fraud caused by diluting the product with inferior products by forgers. In general, quantitative detection methods comprise providing an internal or external control to evaluate the efficiency of detection from one sample/analysis to the next. The efficiency of detection may be affected by many parameters such as, probe hybridization conditions, molecules or substances in the product which may interfere with detection, and/or primer integrity, enzyme quality, temperature variations for detection methods utilizing PCR. By providing a control, in the detection methods, any variable conditions can be normalized to obtain an accurate final concentration of the nucleic acid tag in the product. In certain embodiments a plurality of nucleic acid tags with varying sequences associated with a corresponding plurality of optical reporters may be used in labeling a single item. The different nucleic acid tags can be detected qualitatively by the plurality of optical reporters, each with a different emission wavelength linked to a unique sequence nucleic acid taggant.

In other embodiments of the invention, the methods for authenticating an item comprise labeling the item with an optical reporter marker linked to a nucleic acid tag, detecting the optical reporter, and then characterizing or verifying the nucleic acid taggant associated with the item in an effective manner, by nucleic acid sequencing, genotyping or like techniques. This embodiment allows for verification of tagged items in a manner that's helps prevent forgers counterfeit producers from substituting false or counterfeit goods in place of authentic items.

In an embodiment, a method for authenticating an item with a nucleic acid-linked optical reporter marker in accordance with the invention is provided. The method includes providing an optical reporter marker having a nucleic acid taggant linked to an optical reporter particle, the nucleic acid taggant having a known portion of its sequence identifiable or sequenceable.

A method for authenticating an item further comprises, applying or introducing the nucleic acid-linked optical reporter marker to an item of interest in event. The nucleic acid-linked optical reporter marker may be applied in a specific, predetermined amount or quantity. The item may be labeled with an optical reporter marker throughout the complete item, as a coating over the entire item, or only in a predetermined region or portion of the item. The marker may be applied in liquid solution, liquid dispersion, paste, powder, or other form. Application of the marker may be carried out using an eye-dropper, spoon, spatula, syringe, or other applicator tool. When the item to be authenticated is a solid, a specified amount of optical reporter marker maybe incorporated throughout the volume of the item, or only on the surface of the item or, in some embodiments, placed only on a previously designated section or portion of the item.

In embodiments where the item to be authenticated is a fungible powder, the nucleic acid-lined optical reporter may be dispersed throughout the powdered material.

If the item is a textile or garment item, the marker could be either solid or liquid form of ink and applied to a predetermined area of the garment. Textiles may have a label with the manufactures name on it and may also be used as a region of the garment which the optical reporter marker is placed. The marker may be introduced, for example, by applying a liquid solution or suspension of the marker onto a selected portion of the garment and allowing the solution or suspension to dry by solvent evaporation to leave the markers in place. The marker can also be introduced by applying a binding solution containing DNA marker to the garment.

In embodiments where item to be authenticated is an ink, paint or pigment that may be in liquid, powder or gel form, the nucleic acid labeled optical reporter may be introduced to the ink at a desired concentration and intermixed with the ink as noted above. The ink may be present in a container or cartridge when the nucleic acid marker is added, or the labeled ink may be subsequently transferred into printer cartridges, pens for signing documents, into official stamp ink pads or blotting pads such as utilized by a notary, spray containers, or other containers. Where the item to be authenticated is a printed item such as a document or lithographic print, the nucleic acid-labeled ink may be applied to the document by various print transfer techniques, or by brushing, spraying, blotting or other method of applying ink to a document.

The authentication method further comprises, detecting the nucleic acid-linked optical reporter tag associated with the item of interest. Usually the detecting of the optical reporter marker associated with the item occurs after a period of time has lapsed. For example, after tagging the marked item may be introduced into a supply chain or the item may be placed into service. Frequently, forgers have the best access to items when they are being shipped from the manufacturer/producer to a retail outlet or location. Forgers also have access to the items of interest during maintenance or service of certain of products, such as aircraft, where the item of interest is inspected or replaced (i.e. fasteners). Having a method in which the producer can track and authenticate items or goods allows for a better monitoring of when and where counterfeit goods are being replaced with forgeries or otherwise being tampered with.

Detecting the optical reporter particle(s) represents a first level of authentication of the item. When the optical reporter particle is an upconverting phosphor particle, the marker can be detected by a high energy invisible light source such as an infrared laser, which may be hand-held and manipulated by a user, or suitably mounted to allow goods to be positioned in the lamp output. The infrared light is absorbed by the optical reporter particles, which in turn emit light at a wavelength that is characteristic of the optical reporter particle. Various upconverting phosphor compositions that provide selectable output wavelengths are known in the art, as described further below, and may be used with the invention. Once the optical reporter has been located within or on the item of interest, obtaining a sample of the optical reporter marker may occur.

Next, a sample is collected from the item of interest having the optical reporter marker. In certain embodiments, this may comprise visually inspecting the marker compound, and/or scraping, cutting or dissolving a portion of the marked item to obtain a sample for analysis. When the item has entered a supply chain or has been in service, a manufacturer or an authorized individual can collect a sample of the optical reporter marker from the item at any desired point along the supply chain or during the service or routine maintenance of an item where the item is utilized for authentication purposes. The collecting of the sample may be carried out, for example, by wiping the item with a cloth (which may be moistened with solvent) to remove the marker from the item. The sample collecting in other embodiments may be achieved using a cutting, gouging, scraping, abrading, or other sampling tool configured to remove a portion of the item containing the optical reporter marker.

In an embodiment, the method further includes analyzing the collected sample for the presence of the nucleic acid taggant. In many embodiments the analyzing of the collected sample comprises determining the DNA sequence of the nucleic acid taggant, and comparing the determined DNA sequence with a known or reference DNA sequence. The analysis of the sample collected from the item may occur without further purification, but in many embodiments some form of extraction, isolation or purification of the nucleic acid tag obtained in the sample may be required. Details on the extraction, concentration and purification techniques useful for the methods of the invention are described in more detail above.

In general, the analyzing the sample may be performed by providing a "detection molecule" configured to the nucleic acid tag and using detection methods such, as for example, real time PCR in similar fashion as described above.

The results of the analysis of the collected sample are reviewed and a query or determination is made in similar fashion as discussed above as to whether or not the specific nucleic acid taggant was detected in the sample. If a determination is that an item is not authentic, a different, earlier point in the supply or commerce chain may be selected and then the steps of detecting the optical reporter marker, and the collecting and analyzing a sample may be repeated in similar fashion as discussed above to obtain the time and/or location of tampering or counterfeit substitute.

One embodiment of the present invention, provides a method of marking an item with a DNA marker for authenticating or tracking. The method includes providing an item for marking and applying a medium comprising a DNA marker to the item. The DNA marker encodes information unique to the item.

DNA markers can be embedded in any suitable media for printing that is compatible with a printer ink or toner, or a varnish, or a monomer and polymer combination, or other coating agent, that may be suitable for 3D printing, such as for instance, thermoplastics, thermosets, elastomers, epoxy resins, phenolics, nylon, polyethylene, polystyrene, urethanes and polyurethanes, acrylics and polyacrylates such as for instance cyanoacrylates. See U.S. Pat. No. 7,115,301 for methods of incorporation of DNA markers into non-aqueous media and U.S. patent application Ser. No. 13/648,594 filed Oct. 10, 2012 entitled "Use of Perturbants to Facilitate Incorporation and Recovery of taggants from Polymerized Coatings."

DNA markers can be incorporated into inks, such as permanent marker inks, fountain pen inks and rollerball inks (for instance for high quality pens), as well as felt tip pen ink and colored inks and tints. DNA markers can also be incorporated into solid writing and drawing inks, such as for instance inksticks used traditionally in Far Eastern cultures for calligraphy and brush painting. Inksticks are composed mainly of soot and animal glue, though incense or medicinal scents can be added. To make ink from the inkstick, it is ground against an inkstone with a small quantity of water to produce a dark ink which is then applied with an ink brush. Artists and calligraphists vary the thickness of the resulting ink according to their preference by reducing or increasing the intensity and time of ink grinding.

DNA marking of an item can be accomplished by any suitable method, such as affixing, printing, molding, varnishing, stamping, painting, coating or labeling. For example, suitable printing methods include without limitation, laser jet printing, inkjet printing, Videojet printing, standard printed electronics methods, lithography, flexography, dye transfer printing, laser printing, pad printing, relief printing, rotogravure, screen printing, intaglio printing, offset printing, letterpress printing, electro photography, thermal printing, line printing, dot matrix printing, daisy wheel printing, blueprint printing, solid ink printing, 3D printing, and gang-run printing.

In one embodiment, a DNA marker may be incorporated into or onto items such as, for example, badges, logos, other indicia, etc and these items that include the DNA marker associated therewith can then be affixed to a product for example, an item of clothing, such as for instance a jacket, a sweater or a shirt using methods such as those described in US Patent Application Publication No. US 2008/0293052.

In another embodiment, the present invention provides a method of marking an item with a DNA marker for authenticating or tracking, the method includes: providing a medium including a DNA marker, and molding the medium including the DNA marker to provide all or part of the item to be marked. The DNA marker incorporated into the medium of all or part of the item to be marked can encode information unique to the item.

Suitable molding methods include, for example, blow molding, compaction and sintering, expanded bead molding, extrusion molding, foam molding, injection molding, laminating, reaction injection molding, matched molding, matrix molding, plastic molding, pressure plug assist molding, rotation molding (rotomolding), transfer molding, thermoforming, vacuum forming (a simplified system of thermoforming), vacuum plug assist molding and conformal coating to name but a few. DNA marking of an item according to the methods of the present invention can also be accomplished by painting the DNA onto the item with a brush or stylus. Alternatively, the DNA can be marked by dipping all or part of the item into a DNA-containing coating solution, or into a DNA-infused medium.

The printing or molding of the DNA-containing medium into or onto the item to be marked can be by any suitable molding or printing device that may be available for aerospace, military, material packaging, industrial assembly, medical device, electronic industries among many others. These devices include for instance, and without limitation, Rework Systems available from the Kurz Ersa Corporation (Kurz Ersa, Plymouth, Wis.), from hybrid rework systems that unify all essential process steps in one system for manual operation up to automatic soldering, desoldering and placement, to larger machines with the added features of larger rework systems in compact bench top packages and industrial size manufacturing machines. (See http://www.ersa.com/smt-bga-rework-en.html); Techcon Systems—Adhesive dispensing and fluid dispensing machinery (See http://www.ok-international.com/techcon) for industrial dispensing syringes, cartridges and fluid dispensing tips and adhesive dispensing, liquid dispenser and epoxy dispenser systems for many diverse applications, including for instance, medical device manufacturing applications allowing manufacturers to improve efficiency in their production processes while still staying compliant with requirements of the various regulatory agencies. These fluid applications in production processes include adhesive applications, epoxies, lubricants, coating fluids and reagents and silicones to name but a few, which can be delivered by syringe, needle, micro-needle, or spray, controlled by accurate linear, rotary or spray valves.

Manufacturing of custom rubber molded articles and custom printing with proprietary additives, such as the DNA markers of the present invention is widely available (See for instance http://tekmolding.com/ TechCom of Sussex, N.J. and http://www.padprintmachinery.com/ Pad Print Machinery of Vermont; East Dorset, Vt.).

Items suitable for marking with DNA markers can be any item, whether mass produced or custom manufactured, such as for instance electronic components, mechanical parts, mechanical engineering components, medical supplies, weapons and ammunition, and even commodity items such as chemicals, metals, plastics and paper.

Electronic components suitable for marking with DNA markers can be any electronic component, such as for instance computer chips, integrated circuit chips, capacitors, resistors, transistors, batteries, motherboards and assembly boards as well as sensors (e.g. pressure sensors, temperature sensors, humidity sensors, light sensors, motion sensors, magnetic field sensors, vibration sensors and sensors for the detection of any physical change in the environment).

Mechanical parts components suitable for marking with DNA markers can be any mechanical parts, such as automotive, marine or aviation mechanical parts, generator mechanical parts, turbine mechanical parts, gasoline or diesel engine mechanical parts. Alternatively, the mechanical parts can be for instance fasteners, connectors, screws, nails, nuts and bolts, metal wire, insulated wire, cable, ball bearings, o-rings, brake shoes or any other mechanical parts. Other automotive parts suitable for marking with DNA markers include for instance brake shoes and windshield and window glass, as well as lamp glass and light bulb glass.

Medical supplies suitable for marking with DNA markers can be any medical supplies such as for instance diagnostics, pharmaceuticals, medical devices, catheters, syringes and any other medical equipment or supplies.

Weapons and ammunition suitable for marking with DNA markers can be any weapons or ammunition, such as for instance, firearms, explosives, grenades, shells, bombs, fuses and detonators. Alternatively, the item suitable for marking with DNA markers can be a defensive item such as body armor, vehicle armor plating, armored glass, molded carbon fiber components etc.

The disclosures of each of the patents and published patent applications and non-patent references disclosed herein are each hereby incorporated by reference herein in their entireties.

Having described exemplary embodiments of the present invention, it is further noted that it is readily apparent to those of ordinary skill in the art that various modifications may be made without departing from the spirit and scope of the invention which is defined by the metes and bounds of the appended claims.

We claim:

1. A method of marking an item with a DNA marker for authenticating or tracking, the method comprising:
   providing an item for marking; and
   applying a medium comprising an alkaline activated DNA marker and an optional optical and/or chemical reporter and/or an optional digital reporter to the item, wherein the DNA marker encodes information unique to said item, wherein the alkaline activated DNA is produced by exposing the DNA to an alkaline solution;
   the alkaline solution comprising an alkali metal hydroxide at a concentration in a range from about 0.1 M to about 1.0 M.

2. The method according to claim 1, wherein the applying is by affixing, printing, varnishing, stamping, painting, coating or labeling.

3. The method according to claim 2, wherein the printing is selected from the group consisting of laserjet printing, inkjet printing, Videojet printing, standard printed electronics methods, lithography, flexography, dye transfer printing, laser printing, pad printing, relief printing, rotogravure, screen printing, intaglio printing, offset printing, letterpress printing, electro photography, thermal printing, line printing, dot matrix printing, daisy wheel printing, blueprint printing, solid ink printing, 3D printing, and gang-run printing.

4. The method according to claim 1, wherein the medium comprising the alkaline activated DNA marker is an ink.

5. The method according to claim 1, wherein the medium comprising the alkaline activated DNA marker is a coating medium.

6. The method according to claim 1, wherein the medium comprising the alkaline activated DNA marker further comprises a cyanoacrylate.

7. The method according to claim 1, wherein the alkaline activated DNA marker is bound to an upconverting phosphor (UCP) particle.

8. The method according to claim 7, wherein the alkaline activated DNA marker is bound to the upconverting phosphor (UCP) particle by a linker.

9. The method according to claim 1, wherein the item is marked with an optical reporter in addition to the alkaline activated DNA marker.

10. The method according to claim 9, wherein the optical reporter is a colored dye.

11. The method according to claim 10, wherein the colored dye is part of a design, a trademark, an emblem or a logo.

12. The method according to claim 1, wherein the item is an electronic component selected from the group consisting of a computer chip, an integrated circuit chip, a capacitor, a resistor, a transistor, a sensor, a battery, a motherboard and an assembly board.

13. The method according to claim 1, wherein the item is a flat screen TV, a computer product, an audio player, a smartphone, a disk loaded with a computer program, a CD, a DVD, a BluRay disk, a printed textile or a bank note.

14. The method according to claim 12, wherein the sensor is selected from the group consisting of a pressure sensor, a temperature sensor, an humidity sensor, a light sensor, a motion sensor, a magnetic field sensor and a vibration sensor.

15. The method according to claim 1, wherein the item is a currency note, a coin, a check, or a paper financial instrument.

16. The method according to claim 1, wherein the item is a pharmaceutical, a medicine or a remedy.

17. The method according to claim 1, wherein the item is a fabric, a designer clothing item or a clothing accessory.

18. The method according to claim 1, wherein the item is a household product or an automotive part.

19. A method of marking an item with a DNA marker for authenticating or tracking, the method comprising:
   providing a medium comprising an alkaline activated DNA marker; and
   molding the medium comprising the DNA marker to provide all or part of the item, wherein the DNA marker encodes information unique to said item, wherein the alkaline activated DNA is produced by exposing the DNA to an alkaline solution;
   the alkaline solution comprising an alkali metal hydroxide at a concentration in a range from about 0.1 M to about 1.0 M.

20. The method according to claim 19, wherein the molding is by a method selected from the group consisting of blow molding, compaction and sintering, expanded bead molding, extrusion molding, foam molding, injection molding, laminating, reaction injection molding, matched molding, matrix molding, plastic molding, pressure plug assist molding, rotomolding, transfer molding, thermoforming, vacuum forming, vacuum plug assist molding and conformal coating.

* * * * *